(12) United States Patent
Wayman et al.

(10) Patent No.: US 8,075,523 B2
(45) Date of Patent: Dec. 13, 2011

(54) PASSIVE REUSE PREVENTION SYRINGE THAT USES A TIP LOCK

(75) Inventors: Brian H. Wayman, Morris Plains, NJ (US); Robert Odell, Franklin Lakes, NJ (US); Richard James Caizza, Vernon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 6 days.

(21) Appl. No.: 12/492,524

(22) Filed: Jun. 26, 2009

(65) Prior Publication Data

US 2010/0274190 A1 Oct. 28, 2010

Related U.S. Application Data

(60) Provisional application No. 61/172,866, filed on Apr. 27, 2009.

(51) Int. Cl.
*A61M 5/00* (2006.01)
(52) U.S. Cl. ......... 604/110; 604/187; 604/222; 604/218
(58) Field of Classification Search .................. 604/110, 604/187, 218, 221, 222, 228
See application file for complete search history.

(56) References Cited

U.S. PATENT DOCUMENTS

| | | | |
|---|---|---|---|
| 4,747,830 A | 5/1988 | Gloyer et al. | |
| 4,888,002 A * | 12/1989 | Braginetz et al. | 604/195 |
| 4,986,812 A | 1/1991 | Perler | |
| 5,047,017 A | 9/1991 | Koska | |
| 5,125,899 A | 6/1992 | Frignoli | |
| 5,205,824 A * | 4/1993 | Mazur | 604/110 |
| 5,211,630 A | 5/1993 | Schmahmann | |
| 5,527,284 A | 6/1996 | Ohnemus et al. | |
| 5,531,693 A | 7/1996 | Vounatsos | |
| 5,562,623 A | 10/1996 | Shonfeld et al. | |
| 5,814,017 A | 9/1998 | Kashmer | |

(Continued)

FOREIGN PATENT DOCUMENTS

EP 1106194 6/2001

(Continued)

OTHER PUBLICATIONS

Photos of Kojak Selinge (Star Syringe K1) Auto-Disable Syringe with Disposable Needle.

(Continued)

*Primary Examiner* — Nicholas Lucchesi
*Assistant Examiner* — Leah Stohr
(74) *Attorney, Agent, or Firm* — Jeanne P. Lukasavage; The Webb Law Firm

(57) ABSTRACT

Various embodiments of syringe assemblies include a syringe barrel and a substantially conical tip or outlet disposed on the distal end of the barrel. The substantially conical tip includes a locking mechanism that engages an extension of a plunger assembly extending from a distal end of the plunger assembly so as to retain the extension within the substantially conical tip or outlet upon full injection of the contents of the syringe to a patient. According to one embodiment, a plunger head of the plunger assembly is slidably disposed on the extension. According to another embodiment, a separate hub, which holds a needle cannula, is disposed on an outlet at the distal end of the syringe barrel, which contains the locking mechanism. According to a further embodiment, the locking mechanism includes a locking clip disposed within the substantially conical tip of the syringe assembly.

21 Claims, 22 Drawing Sheets

U.S. PATENT DOCUMENTS

| | | | |
|---|---|---|---|
| 6,117,112 A | 9/2000 | Mahurkar | |
| 6,165,153 A * | 12/2000 | Kashmer | 604/110 |
| 6,267,749 B1 * | 7/2001 | Miklos et al. | 604/110 |
| 6,368,306 B1 | 4/2002 | Koska | |
| 6,790,197 B2 | 9/2004 | Kosinski et al. | |
| 7,282,042 B2 | 10/2007 | Wang | |
| 7,285,110 B2 * | 10/2007 | Fitzgerald | 604/110 |
| 2004/0102737 A1* | 5/2004 | Wu | 604/218 |
| 2004/0147875 A1 | 7/2004 | Wallace et al. | |
| 2005/0038394 A1 | 2/2005 | Schwarzbich | |
| 2005/0159705 A1 | 7/2005 | Crawford et al. | |
| 2006/0064060 A1 | 3/2006 | Lin | |
| 2007/0073223 A1* | 3/2007 | Huang | 604/110 |
| 2007/0106226 A1 | 5/2007 | Croll et al. | |
| 2007/0191785 A1 | 8/2007 | Barere et al. | |
| 2007/0299395 A1 | 12/2007 | Pelkey et al. | |
| 2008/0300550 A1 | 12/2008 | Schiller et al. | |
| 2009/0048560 A1 | 2/2009 | Caizza et al. | |
| 2009/0076450 A1 | 3/2009 | Caizza et al. | |
| 2009/0131869 A1 | 5/2009 | Caizza et al. | |

FOREIGN PATENT DOCUMENTS

| | | |
|---|---|---|
| WO | 88/10127 | 12/1988 |
| WO | 98/03210 | 1/1998 |
| WO | 2005079893 | 9/2005 |
| WO | 2006097105 | 9/2006 |
| WO | 2008154616 | 12/2008 |
| WO | 2008154630 | 12/2008 |

OTHER PUBLICATIONS

Photos of Neomedic Neoject Auto-Disable Syringe.

Photos of KangKang Autodestruct Syringe.

Photos of Dr. Safe Auto-Destruct Syringe Set.

Kojak Selinge "HMD Injection Procedure" Instruction Sheet, pp. 1-2.

Pictures of 0.5ml safety syringe cady, http://www.emunio.dk/solution/cady/pictures.asp.

* cited by examiner

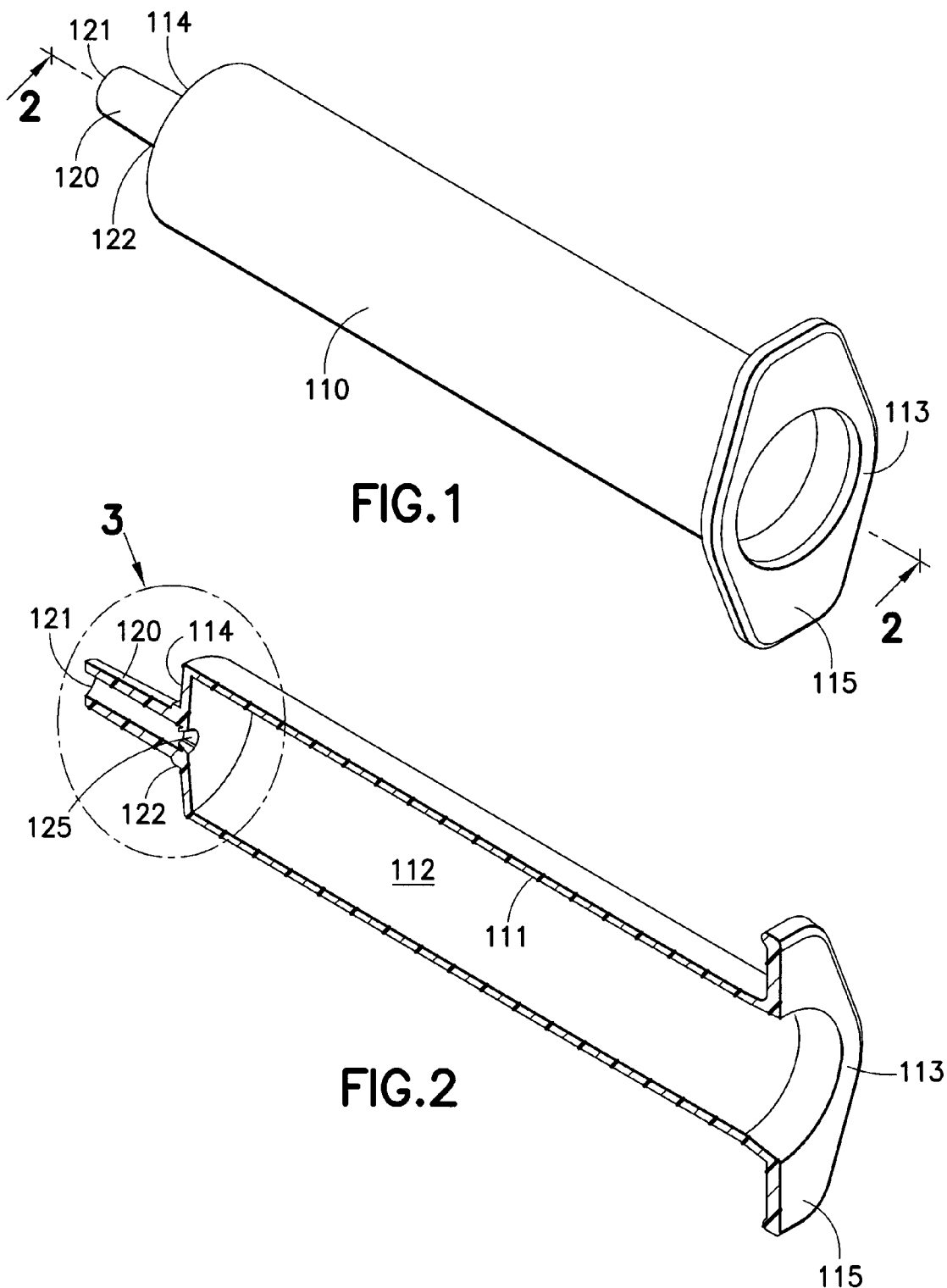

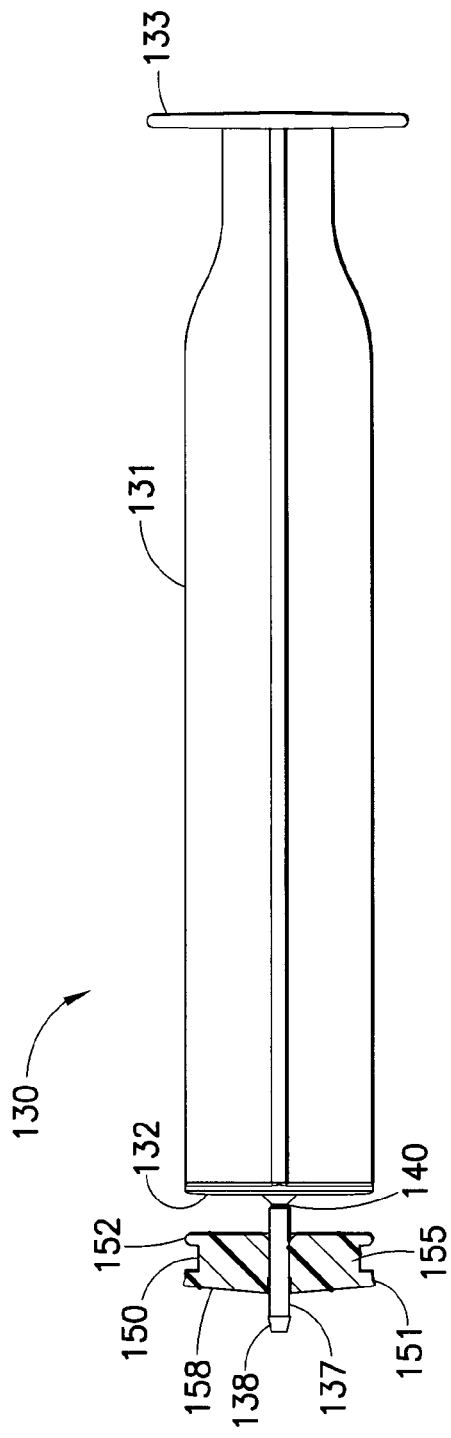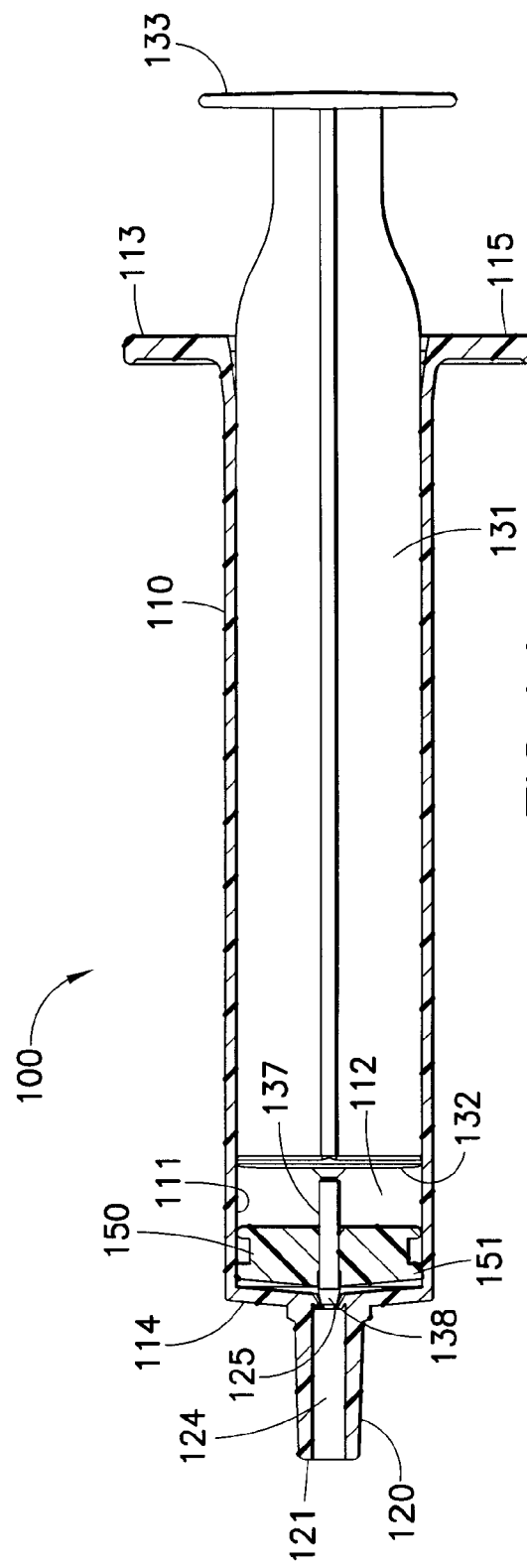

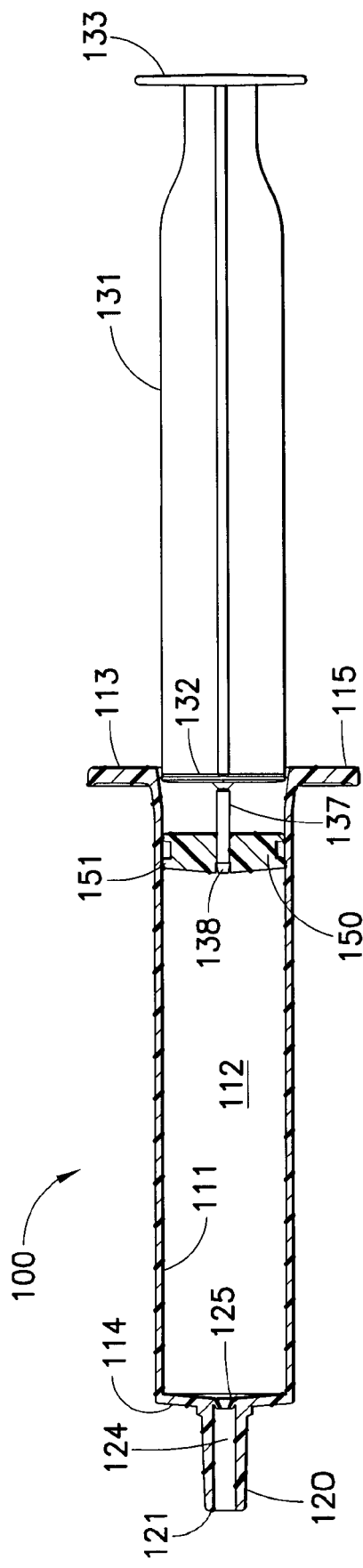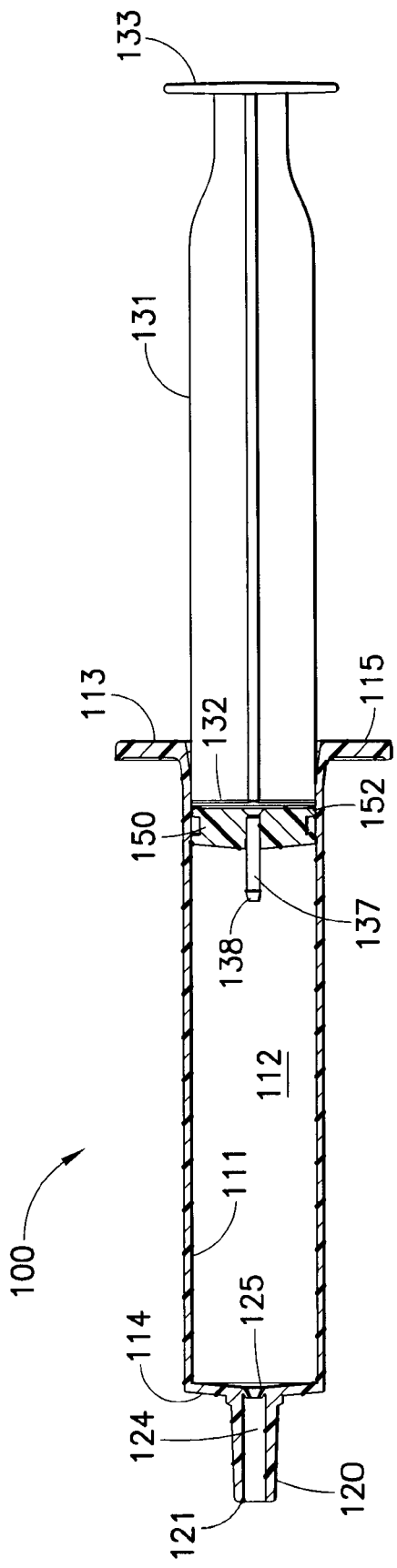

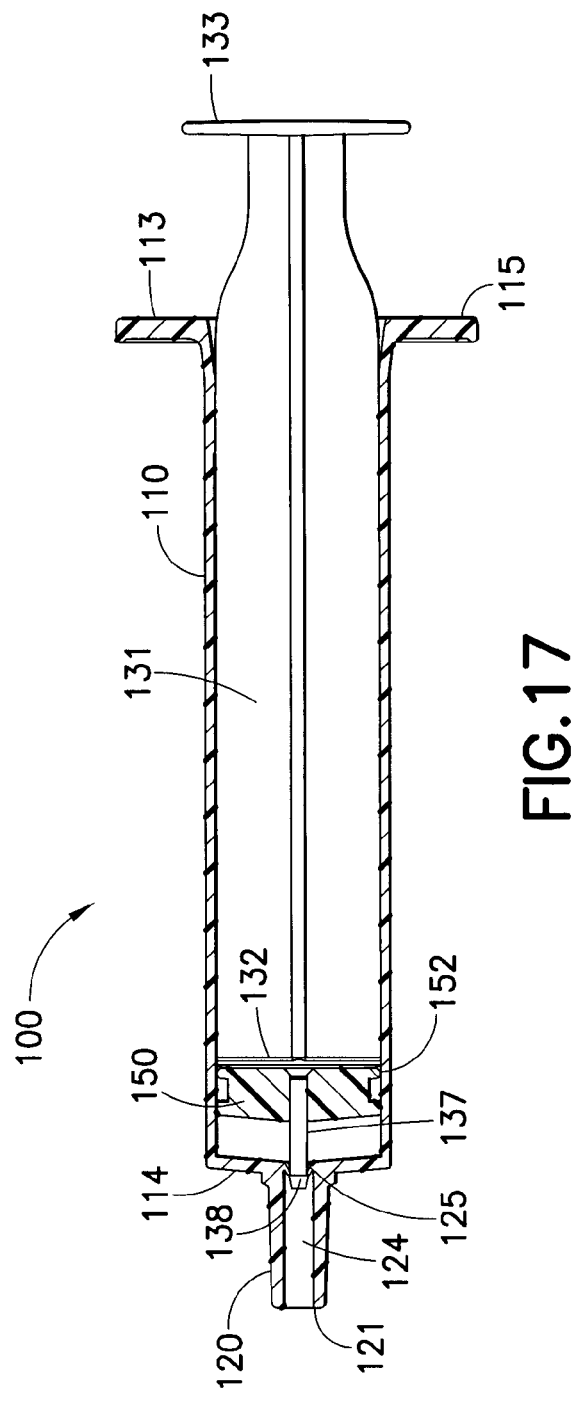
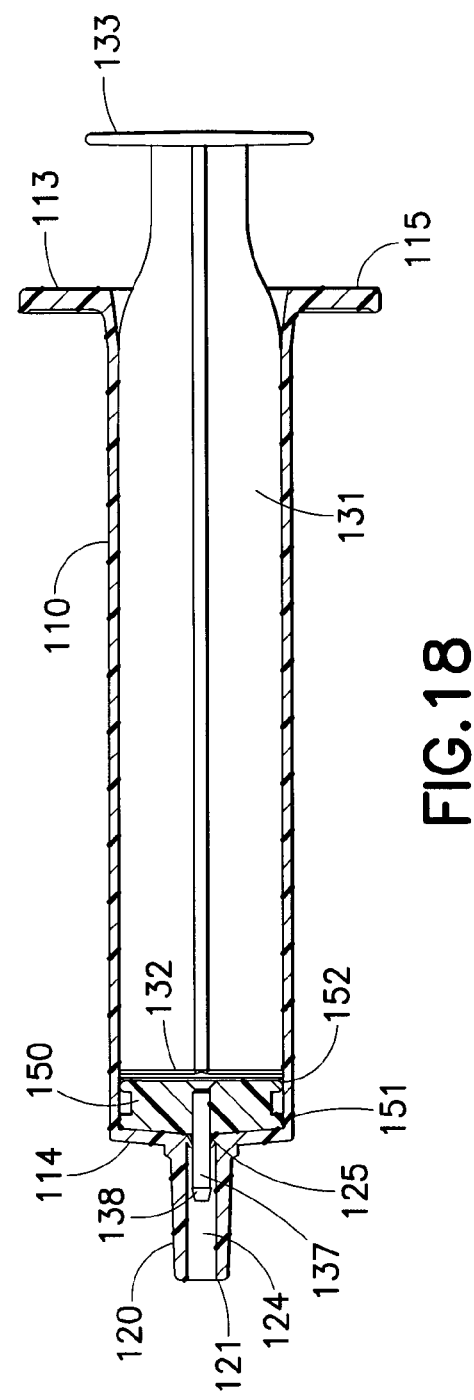

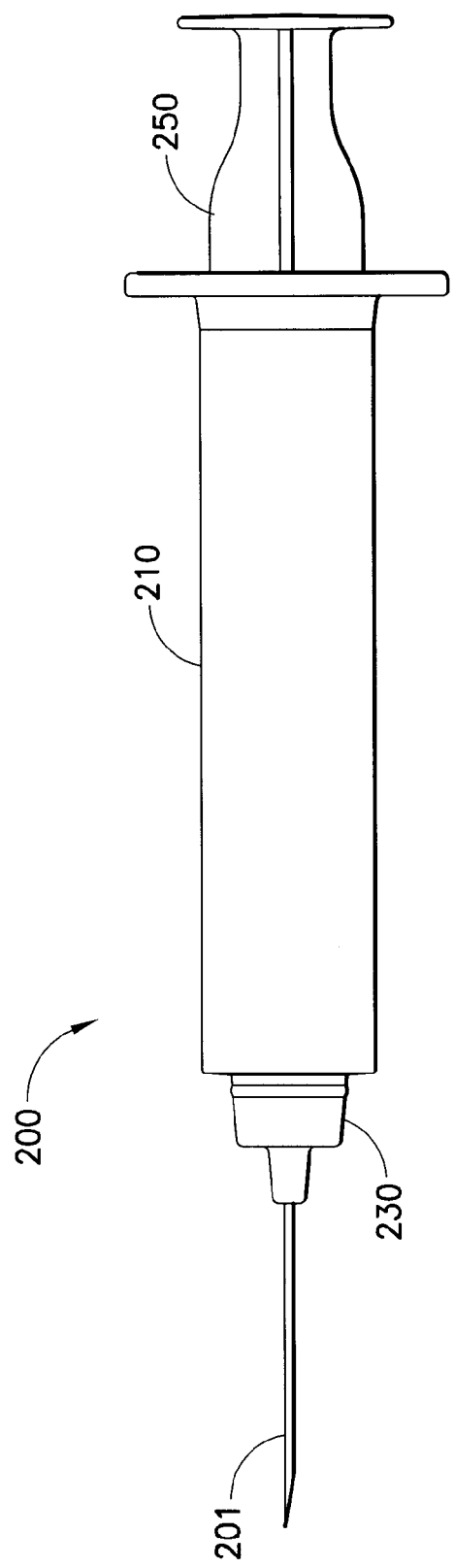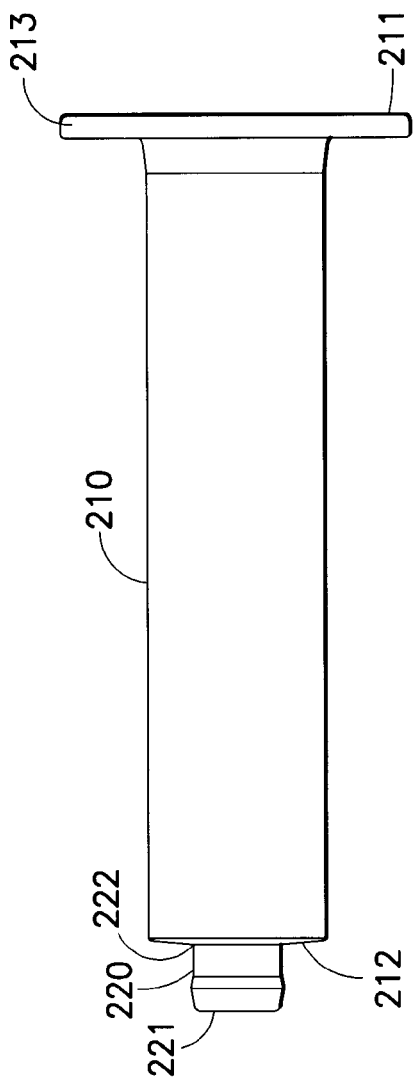

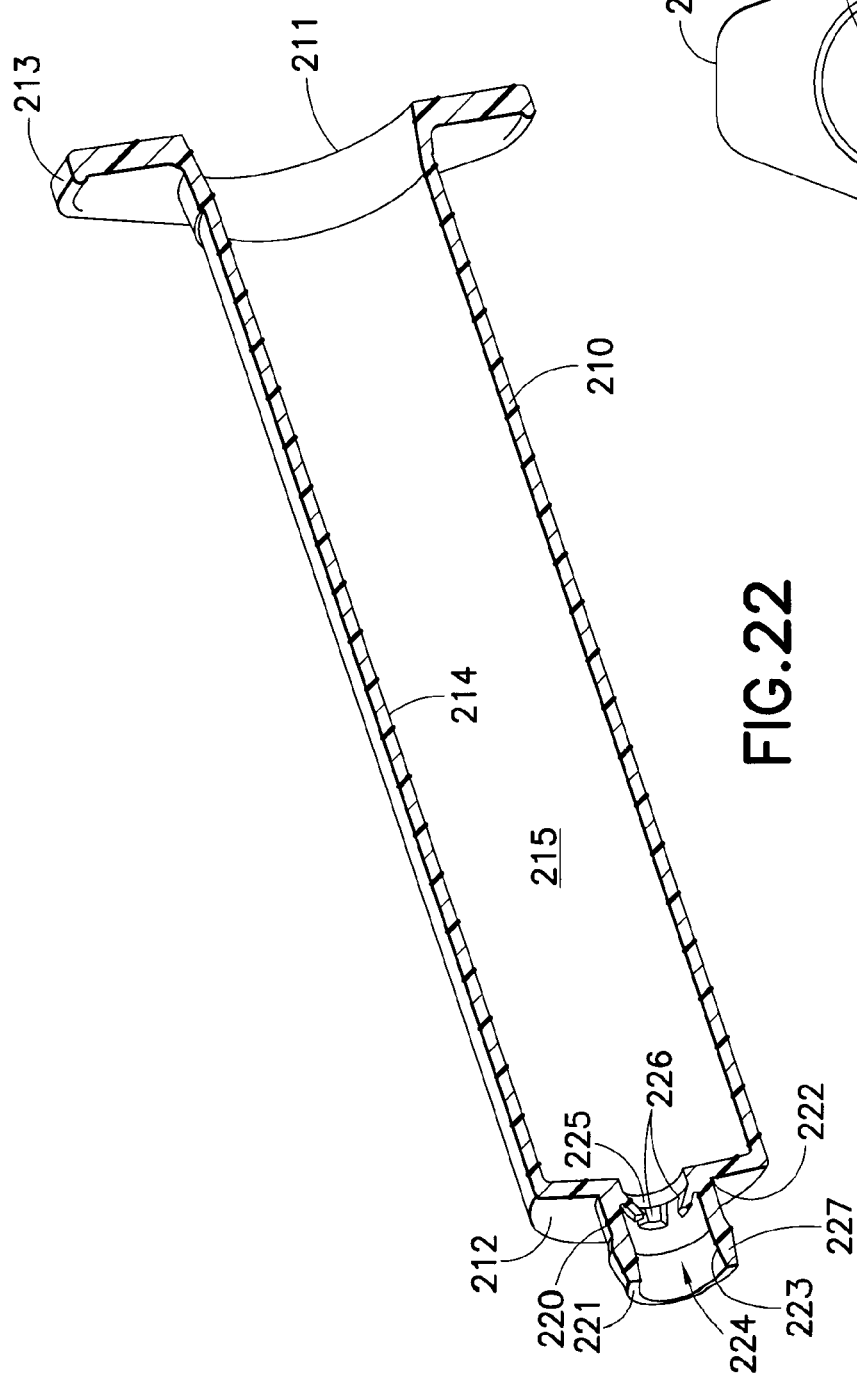
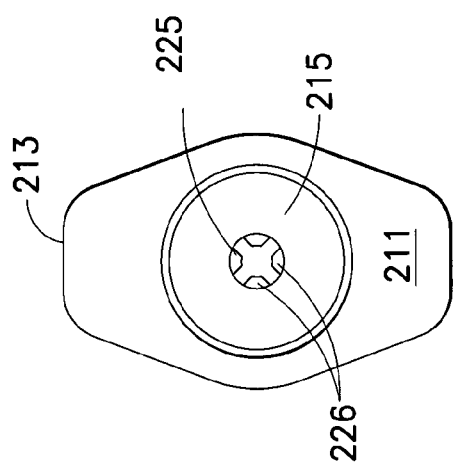
FIG.22
FIG.23

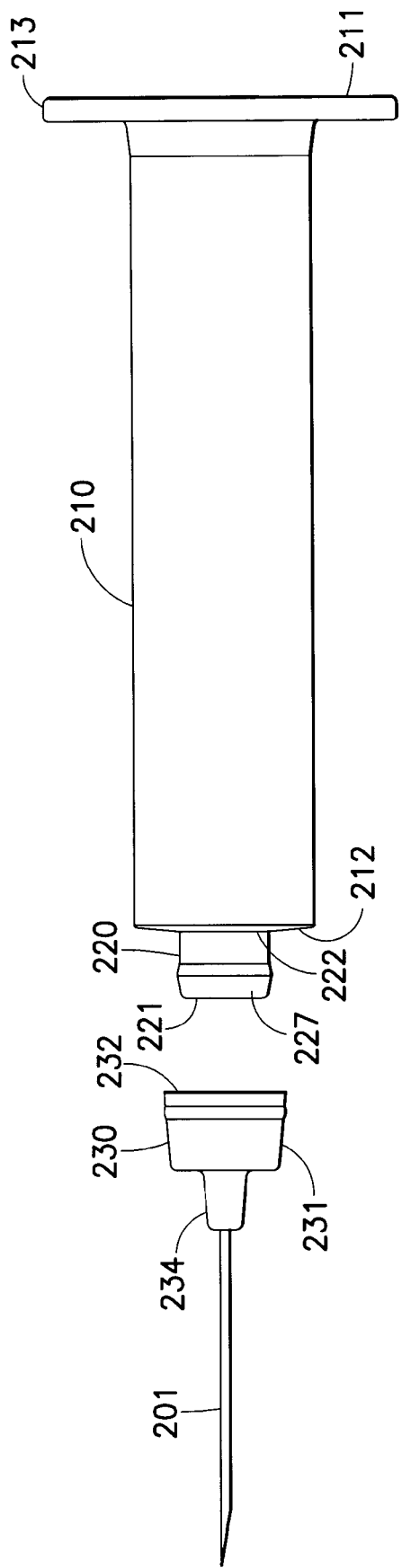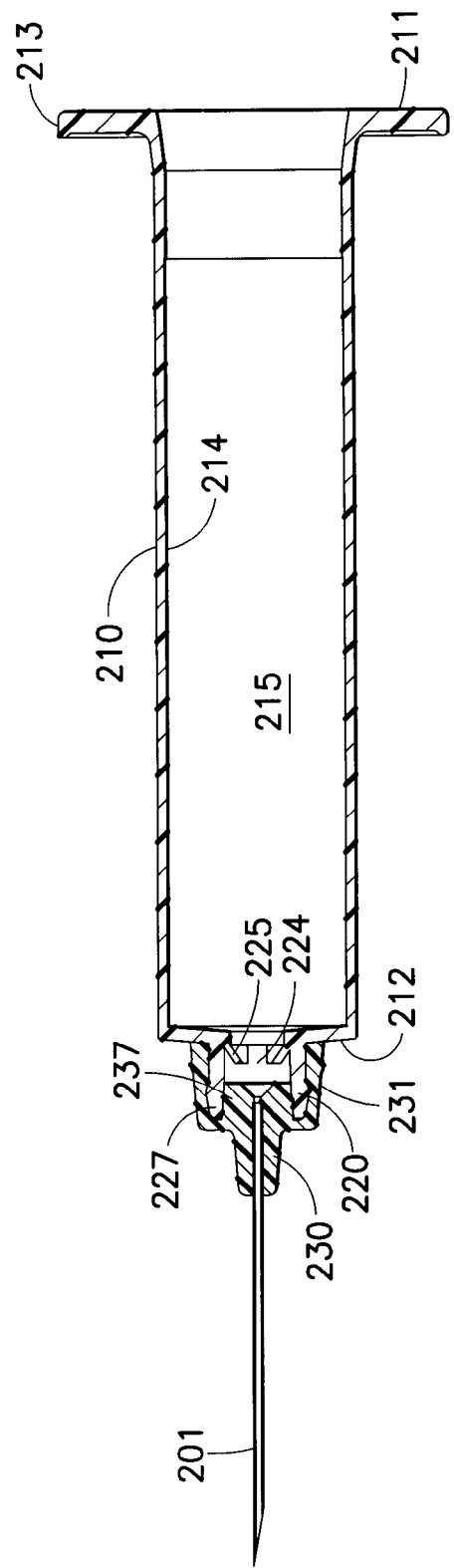
FIG.26
FIG.27

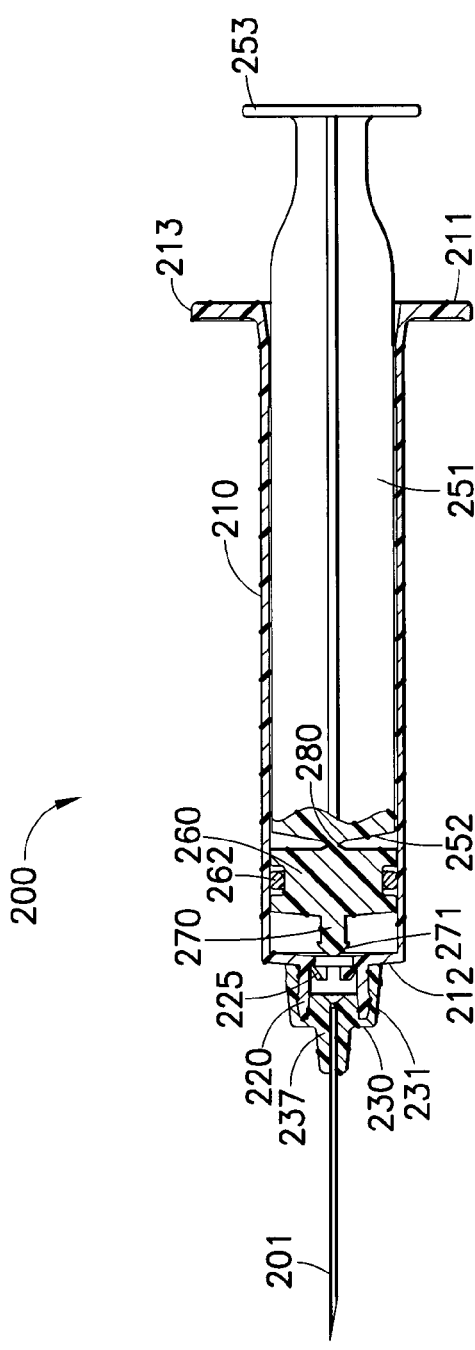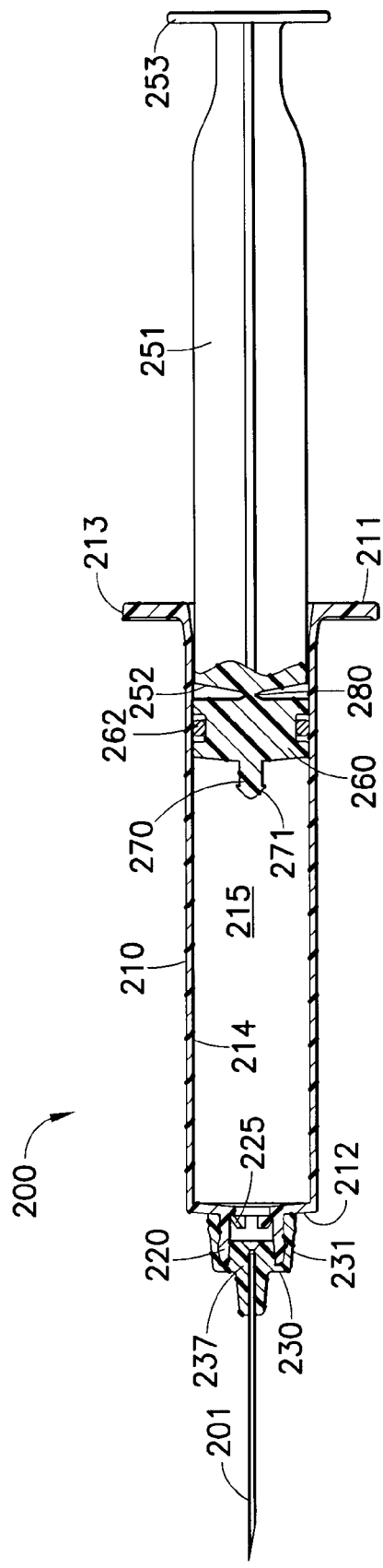

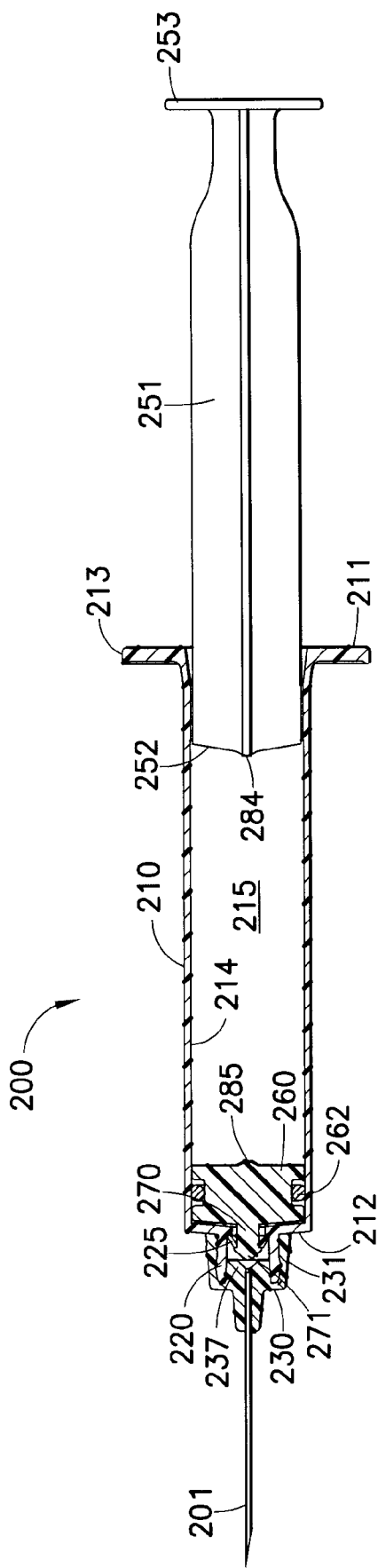
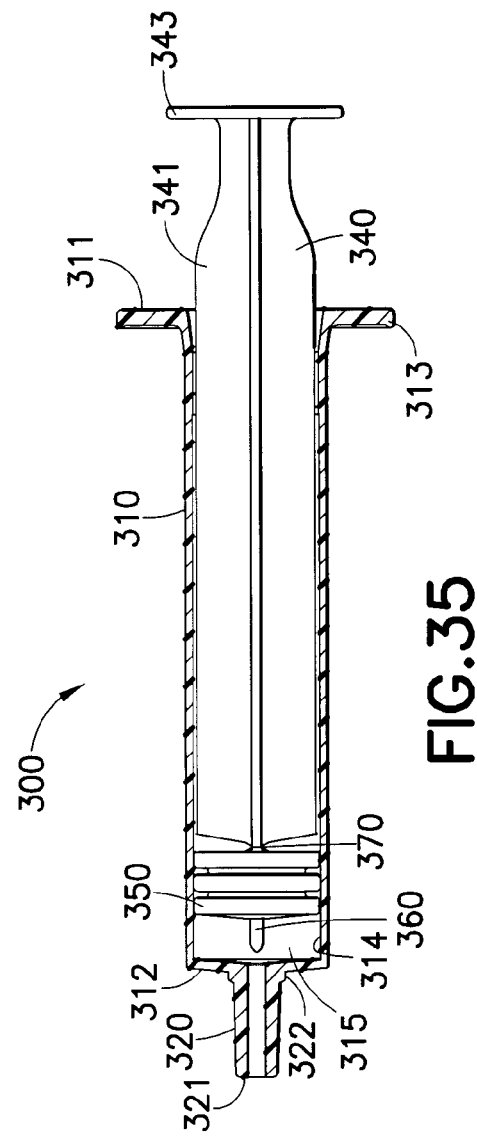
FIG. 34
FIG. 35

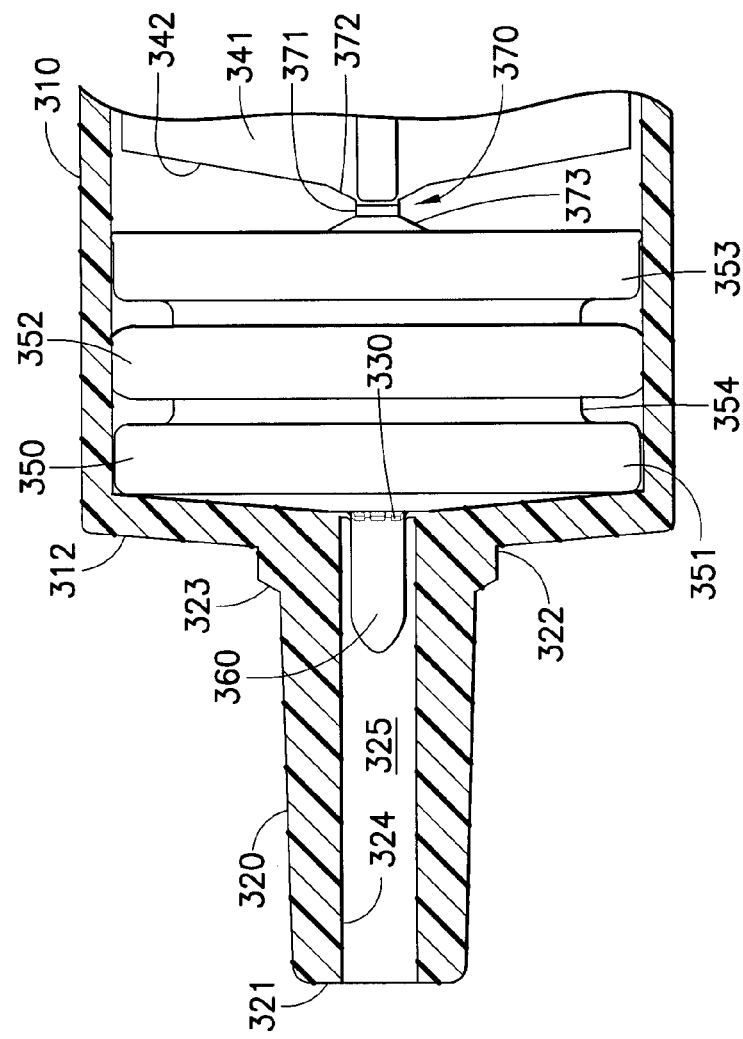

PASSIVE REUSE PREVENTION SYRINGE THAT USES A TIP LOCK

CROSS REFERENCE TO RELATED APPLICATIONS

This application claims priority to U.S. Provisional Application No. 61/172,866 filed on Apr. 27, 2009, the entire contents of which are herein incorporated by reference.

BACKGROUND OF THE INVENTION

1. Field of the Invention

The present invention relates to a passive reuse prevention syringe that uses a luer tip lock. More specifically, aspects of the present invention relate to a syringe that includes a locking mechanism on the inside surface of a luer tip or outlet of a syringe for engaging an extension member extending from a plunger head, which includes the sealing surface of a plunger assembly. After the extension has entered the locked position, attempting to withdraw the plunger assembly from the syringe barrel will result in the plunger assembly breaking into two pieces with the extension remaining in the luer tip of the syringe and the plunger head remaining in the syringe barrel.

2. Description of Related Art

Hypodermic syringe products are generally intended for a single use only, in part, to address concerns related to the spread of disease associated with reuse of such products and to deter other misuse. Attempts have been made to provide a solution to these concerns. Some of these attempts have provided injection systems that require a specific, affirmative act to destroy the syringe after the intended injection either by using a separate device for destroying the syringe or providing a syringe assembly with frangible zones so that the syringe could be rendered inoperable by the application of force. Although many of these devices work quite well, they do require the specific intent of the user followed by the affirmative act to destroy or render the syringe inoperable. These devices are not effective with a user having the specific intent to reuse the hypodermic syringe.

Attempts have also been made to provide a syringe assembly that is automatically disabled or rendered inoperable after a single or select number of uses. Such syringe assemblies present specific challenges because they must not prevent filling or use under normal conditions. Moreover, certain automatic locking and disabling devices only allow for a fixed dosage amount to be supplied by the syringe before the syringe is disabled.

SUMMARY OF THE INVENTION

Accordingly, there is a general need for a single use syringe that includes a locking and disabling mechanism that does not operate automatically but that is passively activated through normal use of the syringe. Consequently, a user who has the specific intent to reuse the syringe will actuate the mechanism through normal use of the syringe without consciously realizing that the syringe has been disabled. Such a mechanism will limit the ability of users to reuse the syringe while avoiding the unnecessary costs and dosage limitations of automatic devices.

Aspects of the present invention provide many advantages over injection systems in the prior art by providing a syringe that offers the utility of a traditional syringe along with reuse prevention features and that requires a low force to activate the reuse prevention mechanism. According to one implementation of the present invention, the syringe includes a passive reuse prevention mechanism that is activated by the user through normal use of the syringe though the user may not be aware or realize that the mechanism has been activated. The syringe allows for variable dosing, which is important for some procedures, but can also be adapted to deliver fixed doses if required and can be used for injections and/or reconstitution of dry drugs. The syringe is scalable from the smallest syringe sizes to the largest syringe sizes and allows for reductions of cost compared to current reuse prevention syringes. The syringe is provided with a plunger assembly having a sealing surface on a plunger head with an extension member of the plunger assembly engaged by the locking mechanism, which is located within the luer tip or outlet of the syringe, such that there is no need for an expensive rubber stopper or plug on the plunger for sealing the syringe barrel, which reduces the material and manufacturing costs. Further, the plunger assembly has a breakable portion integrally molded so that the syringe will become disabled if an attempt is made to reuse the syringe after the extension has entered a locked position.

According to an embodiment of the present invention, a syringe assembly is provided. The syringe assembly includes a syringe barrel having an inside surface defining a chamber; an open proximal end and a distal end; a substantially conical tip disposed on the distal end of the barrel; the substantially conical tip having a distal end, a proximal end, an inside surface defining a passage in fluid communication with the chamber at the proximal end of the substantially conical tip and a locking mechanism disposed within the passage; and a plunger assembly disposed at least partially within the syringe barrel; the plunger assembly including an elongate plunger rod having a distal end surface, an extension disposed on the distal end surface of the plunger rod and having a tip on a distal end thereof; and a plunger head slidably disposed on the extension between the tip of the extension and the distal end surface of the plunger rod, the plunger head having a distal sealing surface. During an injection cycle, the plunger head slides with respect to the extension and the plunger rod such that the plunger head engages the tip of the extension during aspiration and engages the distal end surface of the plunger rod during injection. After completion of the injection cycle, the tip of the extension extends into the passage in the substantially conical tip and engages the locking mechanism so as to prevent removal of the tip of the extension from the substantially conical tip.

The locking mechanism includes a plurality of flexible protrusions disposed about the inside surface of the substantially conical tip and extending into the passage, the flexible protrusions being adapted to flex toward the inside surface of the substantially conical tip so as to allow the tip of the extension to pass between them. The protrusions are disposed at an angle so as to extend toward the distal end of the substantially conical tip. The locking mechanism is disposed within the substantially conical tip at the proximal end of the substantially conical tip. The barrel further includes an outwardly extending flange at the open proximal end thereof.

The extension of the plunger assembly has a length extending from the distal end surface of the plunger rod to the tip of the extension, the length of the extension being greater than a thickness of the plunger head. The tip of the extension tapers outwardly from the distal end of the extension toward the distal end surface of the plunger rod so as to form an abutment surface between the extension and the tip at a widest part of the tip, the tip of the extension being engaged by the locking mechanism at the abutment surface. The tip of the extension has a substantially conical shape and the abutment surface encircles the extension. The extension has a cylindrical shape. The plunger rod includes an outwardly extending flange at a proximal end thereof.

The plunger head further includes a distal wall, the distal wall having the distal sealing surface defined thereon; a proximal wall, spaced from the distal wall; and a central portion extending between the distal wall and the proximal wall, the central portion having a cylindrical core portion and a plurality of equally spaced fin portions extending radially from the cylindrical core portion. The distal wall, the proximal wall, and the cylindrical core portion of the central portion define a hole extending through the plunger head, the extension being received within the hole. The distal wall of the plunger head perimetrically engages the inner surface of the barrel so as to seal the chamber of the barrel. The cylindrical core portion of the plunger head sealingly engages the extension when the extension is received within the hole. A force necessary to advance the plunger rod relative to the plunger head during the injection cycle between aspiration and injection is less than a force necessary to sustain injection.

The extension includes a breakable neck portion proximate to the distal end surface of the plunger rod, the breakable neck portion being adapted to break upon application of a force to the plunger rod that is greater than a force necessary to at least partially aspirate the syringe, and less than a force necessary to withdraw the tip of the extension of the plunger assembly past the locking mechanism of the substantially conical tip.

According to a further aspect of the present invention, a method of actuating a syringe assembly is provided. The method includes the steps of: providing a syringe assembly that includes a syringe barrel having an inside surface defining a chamber, an open proximal end, and a distal end; a substantially conical tip disposed on the distal end of the barrel, the substantially conical tip having a distal end, a proximal end, an inside surface defining a passage in fluid communication with the chamber at the proximal end of the substantially conical tip and a locking mechanism disposed within the passage, a plunger assembly disposed at least partially within the syringe barrel, the plunger assembly including an elongate plunger rod having a distal end surface, an extension disposed on the distal end surface of the plunger rod having a tip on a distal end thereof; and a plunger head slidably disposed on the extension between the tip of the extension and the distal end surface of the plunger rod, the plunger head having a distal sealing surface. The plunger assembly is partially withdrawn from a position proximate to the distal end of the syringe barrel in a proximal direction with the plunger head engaging the tip of the extension so as to aspirate the chamber of the syringe barrel. The plunger assembly is advanced within the chamber of the syringe barrel so that the plunger head slides with respect to the plunger rod and extension and engages the distal end surface of the plunger rod. The plunger assembly is further advanced within the chamber of the syringe barrel. The extension is retained in a locked position at least partially within the passage in the substantially conical tip by engagement between the tip of the extension and the locking mechanism in the passage.

According to a further embodiment of the present invention, a syringe assembly is provided. The syringe assembly includes: a syringe barrel having an inside surface defining a chamber, an open proximal end, and a distal end; a syringe outlet disposed on the distal end of the barrel, the outlet having a distal end, a proximal end, an inside surface defining a passage in fluid communication with the chamber at the proximal end of the outlet, and a locking mechanism disposed within the passage; a hub including a cylindrical skirt portion having an open proximal end and a distal end, and a tip extending from the distal end of the cylindrical skirt portion, the tip of the hub having an orifice extending therethrough in fluid communication with an interior of the cylindrical skirt portion; and a plunger assembly disposed at least partially within the syringe barrel, the plunger assembly including an elongate plunger rod having a distal end surface, a plunger head connected to the distal end surface of the plunger rod and having a distal wall, the plunger head having a sealing member disposed thereon, and an extension disposed on the distal wall of the plunger head and having a tip on a distal end thereof. The cylindrical skirt portion of the hub is disposed on the outlet and forms a mating engagement with the outlet such that the orifice of the hub is in fluid communication with the passage of the outlet. The locking mechanism is adapted to engage and retain the tip of the extension of the plunger assembly in a locked position at least partially within the passage of the outlet, while allowing the plunger rod to be removed from the chamber of the barrel. The barrel further includes an outwardly extending flange at the open proximal end thereof.

The locking mechanism is disposed within the outlet at the proximal end of the outlet. The locking mechanism includes a plurality of flexible protrusions disposed about the inside surface of the outlet and extending into the passage, the flexible protrusions being adapted to flex toward the inside surface of the outlet so as to allow the tip of the extension to pass between them. The protrusions are disposed at an angle so as to extend toward the distal end of the outlet.

The outlet has a cylindrical shape with a distal end portion having an increased diameter tapering outwardly in a direction toward the proximal end of the outlet. The hub further includes a plug portion extending proximally within the cylindrical skirt portion from the distal end of the cylindrical skirt portion so as to form an annular recess between the plug portion and the cylindrical skirt portion, the annular recess being shaped to correspond to a shape of the outside surface of the distal end portion of the outlet and the orifice of the tip of the hub extending through the plug portion. The plug portion of the hub extends into the passage of the outlet of the syringe so as to close the passage and to cause the distal end portion of the outlet to engage the hub within the annular recess in a secured mating engagement. The secured mating engagement between the hub and the outlet is permanently secured.

The orifice includes a substantially conical inlet at a proximal surface of the plug portion of the hub, the substantially conical inlet being shaped to correspond to a shape of the tip of the extension of the plunger assembly. A needle cannula is connected to the hub within the orifice.

The plunger rod includes an outwardly extending flange at a proximal end thereof. The tip of the extension tapers outwardly from the distal end of the extension toward the distal end surface of the plunger rod so as to form an abutment surface between the extension and the tip at a widest part of the tip, the tip of the extension being engaged by the locking mechanism at the abutment surface. The tip of the extension has a substantially conical shape and the abutment surface encircles the extension. The extension has a cylindrical shape.

The plunger head further includes a proximal wall spaced from the distal wall and a central portion extending between the distal wall and the proximal wall, the central portion having a diameter less than a diameter of the distal and proximal walls. The sealing member includes an O-ring disposed around the central portion of the plunger head, the O-ring engaging the inside surface of the barrel so as to seal the chamber.

The plunger head is connected to the distal end surface of the plunger rod by a breakable neck portion, the breakable neck portion being adapted to break upon application of a force to the plunger rod that is greater than a force necessary to at least partially aspirate the syringe, and less than a force necessary to withdraw the tip of the extension of the plunger assembly past the locking mechanism of the outlet. The breakable neck portion includes a center disposed between a proximal wall of the plunger head and the distal end surface of the plunger rod and tapered portions extending from both the proximal end wall of the plunger head and the distal end surface of the plunger rod so as to have a reduced diameter at the center.

According to a further aspect of the present invention, a method of actuating a syringe assembly is provided. The method includes the step of providing a syringe assembly that includes a syringe barrel having an inside surface defining a chamber, an open proximal end, and a distal end; a syringe outlet disposed on the distal end of the barrel, the outlet having a distal end, a proximal end, an inside surface defining a passage in fluid communication with the chamber at the proximal end of the outlet, and a locking mechanism disposed within the passage; a hub including a cylindrical skirt portion having an open proximal end and a distal end, and a tip extending from the distal end of the cylindrical skirt portion, the tip of the hub having an orifice extending therethrough in fluid communication with an interior of the cylindrical skirt portion; and a plunger assembly disposed at least partially within the syringe barrel, the plunger assembly including an elongate plunger rod having a distal end surface, a plunger head connected to the distal end surface of the plunger rod and having a distal wall, the plunger head having a sealing member disposed thereon, and an extension disposed on the distal wall of the plunger head and having a tip on a distal end thereof. The cylindrical skirt portion of the hub is disposed on the outlet and forms a mating engagement with the outlet such that the orifice of the hub is in fluid communication with the passage of the outlet. The plunger assembly is partially withdrawn from a position proximate to the distal end of the syringe barrel in a proximal direction so as to aspirate the chamber of the syringe barrel. The plunger assembly is advanced within the chamber of the syringe barrel. The extension is retained in a locked position at least partially within the passage in the outlet by engagement between the tip of the extension and the locking mechanism in the passage.

According to a further embodiment of the present invention, a syringe assembly is provided. The syringe assembly includes a syringe barrel having an inside surface defining a chamber, an open proximal end, and a distal end; a substantially conical tip disposed on the distal end of the barrel, the substantially conical tip having a distal end, a proximal end, an inside surface defining a passage in fluid communication with the chamber at the proximal end of the substantially conical tip, and a locking clip disposed within the passage; and a plunger assembly disposed at least partially within the syringe barrel, the plunger assembly including an elongate plunger rod having a distal end surface, a plunger head connected to the distal end surface of the plunger rod and having a distal wall, the plunger head having a sealing member disposed thereon, and an extension disposed on the distal wall of the plunger head. The locking clip is adapted to engage and retain the extension of the plunger assembly in a locked position at least partially within the passage of the substantially conical tip, while allowing the plunger rod to be removed from the chamber of the barrel.

The locking clip includes an outer cylindrical ring having an inner circumferential surface and a plurality of fingers extending from the inner circumferential surface into the passage of the substantially conical tip, the fingers being adapted to engage and retain the extension of the plunger assembly. The locking clip is disposed within the substantially conical tip at the proximal end of the substantially conical tip. The locking clip may be made from metal.

The barrel further includes an outwardly extending flange at the open proximal end thereof. The plunger rod includes an outwardly extending flange at a proximal end thereof. The extension has a cylindrical shape.

The plunger head further includes a proximal wall spaced from the distal wall and a central portion extending between the distal wall and the proximal wall, the central portion having a diameter less than a diameter of the distal and proximal walls. The sealing member includes an O-ring disposed around the central portion of the plunger head, the O-ring engaging the inside surface of the barrel so as to seal the chamber.

The plunger head is connected to the distal end surface of the plunger rod by a breakable neck portion, the breakable neck portion being adapted to break upon application of a force to the plunger rod that is greater than a force necessary to at least partially aspirate the syringe, and less than a force necessary to withdraw the extension of the plunger assembly past the locking clip of the substantially conical tip. The breakable neck portion includes a center disposed between a proximal wall of the plunger head and the distal end surface of the plunger rod and tapered portions extending from both the proximal end wall of the plunger head and the distal end surface of the plunger rod so as to have a reduced diameter at the center.

According to a further aspect of the present invention, a method of actuating a syringe assembly is provided. The method includes the steps of providing a syringe assembly that includes a syringe barrel having an inside surface defining a chamber, an open proximal end, and a distal end; a substantially conical tip disposed on the distal end of the barrel, the substantially conical tip having a distal end, a proximal end, an inside surface defining a passage in fluid communication with the chamber at the proximal end of the substantially conical tip, and a locking clip disposed within the passage; and a plunger assembly disposed at least partially within the syringe barrel, the plunger assembly including an elongate plunger rod having a distal end surface, a plunger head connected to the distal end surface of the plunger rod and having a distal wall, the plunger head having a sealing member disposed thereon, and an extension disposed on the distal wall of the plunger head. The plunger assembly is partially withdrawn from a position proximate to the distal end of the syringe barrel in a proximal direction so as to aspirate the chamber of the syringe barrel. The plunger assembly is advanced within the chamber of the syringe barrel. The extension is retained in a locked position at least partially within the passage in the substantially conical tip by engagement between the extension and the locking clip in the passage.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 1 is a perspective view of a syringe barrel and luer tip of a passive reuse prevention syringe in accordance with an embodiment of the present invention.

FIG. 2 is a cross-sectional view of the syringe barrel and luer tip taken along lines 2-2 shown in FIG. 1.

FIG. 13 is a partial cross-sectional side view of the plunger assembly of FIG. 11 with the plunger head disposed on the extension.

FIG. 14 is a partial cross-sectional side view of a passive reuse prevention syringe in accordance with an embodiment of the present invention in an initial state prior to use.

FIG. 15 is a partial cross-sectional side view of the passive reuse prevention syringe of FIG. 14 after aspiration of the syringe.

FIG. 16 is a partial cross-sectional side view of the passive reuse prevention syringe of FIG. 14 prior to the initial injection of the contents of the syringe.

FIG. 17 is a partial cross-sectional side view of the passive reuse prevention syringe of FIG. 14 during injection with the extension entering into a locked position.

FIG. 18 is a partial cross-sectional side view of the passive reuse prevention syringe of FIG. 14 after injection of the contents of the syringe, and with the extension being situated in a locked position.

FIG. 20 is a side view of a passive reuse prevention syringe in accordance with an embodiment of the present invention.

FIG. 21 is a side view of a syringe barrel and outlet of the passive reuse prevention syringe of FIG. 20.

FIG. 22 is a cross-sectional perspective view of the syringe barrel and outlet of FIG. 21.

FIG. 23 is a proximal side view of the syringe barrel and outlet of FIG. 21.

FIG. 26 is a side view of the hub and cannula and the syringe barrel and outlet of the passive reuse prevention syringe of FIG. 20.

FIG. 27 is a cross-sectional side view of the hub and cannula and the syringe barrel and outlet of FIG. 26 with the hub disposed on the outlet.

FIG. 30 is a partial cross-sectional side view of the passive reuse prevention syringe of FIG. 20 in an initial state prior to use.

FIG. 31 is a partial cross-sectional side view of the passive reuse prevention syringe of FIG. 20 after aspiration of the syringe.

FIG. 34 is a partial cross-sectional side view of the passive reuse prevention syringe of FIG. 20 with the locked plunger being broken into two pieces.

FIG. 35 is a partial cross-sectional side view of a passive reuse prevention syringe in accordance with an embodiment of the present invention in an initial state prior to use.

FIG. 42 is an enlarged sectional view of FIG. 41.

FIG. 43 is a partial cross-sectional side view of the passive reuse prevention syringe of FIG. 35 with the locked plunger being broken into two pieces.

DESCRIPTION OF PREFERRED EMBODIMENTS

Figure 3:
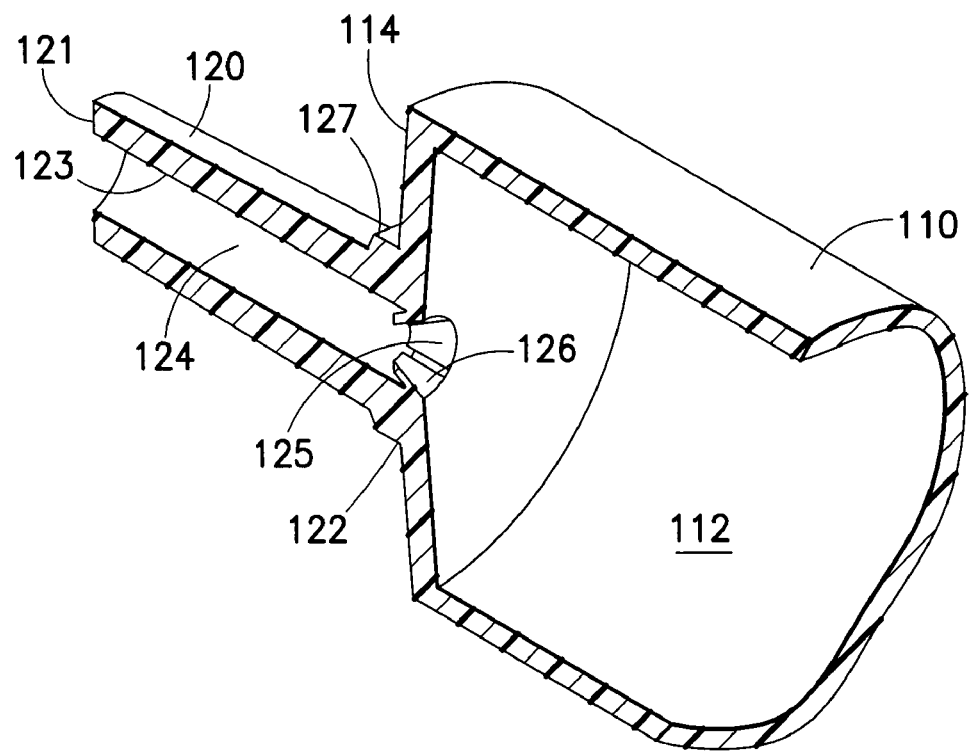
FIG. 3 is an enlarged sectional view of FIG. 2.

For purposes of the description hereinafter, spatial orientation terms, if used, shall relate to the referenced embodiment as it is oriented in the accompanying drawing figures or otherwise described in the following detailed description. The term "proximal" refers to a location nearest the person using the device, and farthest from the patient. Conversely, the term "distal" refers to a location farthest from the person using the device, and closest to the patient. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to FIGS. 1-19, a syringe assembly 100 is shown according to an embodiment of the present invention. The syringe assembly 100 includes a syringe barrel 110 and a luer tip 120 extending from a distal end 114 of the syringe barrel 110. As shown in FIG. 1, the syringe barrel 110 has an open proximal end 113 opposite to the distal end 114 of the barrel 110. The luer tip 120 has a proximal end 122 attached to the distal end 114 of the syringe barrel 110 and a distal end 121 opposite to the proximal end 122 of the luer tip 120. As shown, the syringe barrel 110 and luer tip 120 are integrally formed and may have a cylindrical or substantially cylindrical shape, and may include an outwardly extending flange 115 at the open proximal end 113 of the barrel 110, though it is to be appreciated that the syringe barrel 110 and luer tip 120 may be formed in any suitable shape or formed separately and attached. Additionally, the syringe barrel 110 and luer tip 120 may be injection molded from thermoplastic material such as polypropylene and polyethylene according to techniques known to those of ordinary skill in the art, though it is to be appreciated that the syringe barrel 110 and luer tip 120 may be made from other suitable materials, including glass, and according to other applicable techniques. It is to be appreciated that the term "luer" as used herein is intended to encompass not only those tips that meet the standardized requirements for forming a luer lock connection but any conical or substantially conical tip.

Figure 4:
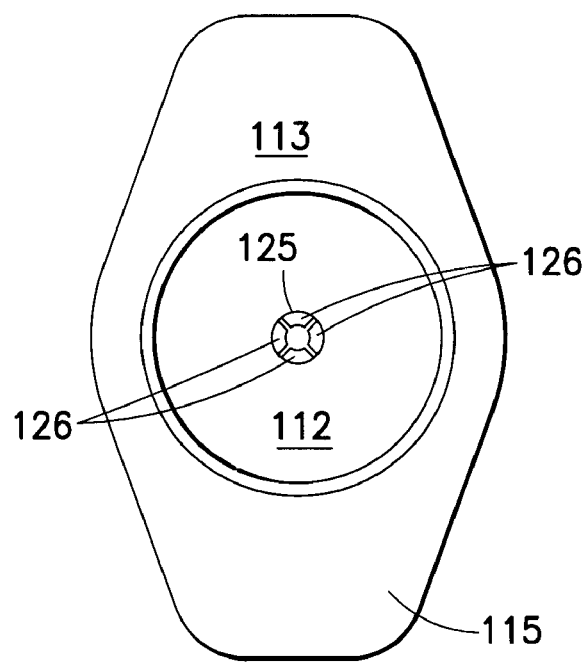
FIG. 4 is a proximal side view of the syringe barrel and luer tip of FIG. 1.

As shown in FIGS. 2-4, the syringe barrel 110 has an inside surface 111 that defines a chamber 112. Also, the luer tip 120 has an inside surface 123 that defines a passage 124 in fluid communication with the chamber 112 of the syringe barrel 110. The passage 124 of the luer tip 120 may be sized to receive a needle cannula (such as needle cannula 201, shown in FIG. 20) therein. Alternatively, the luer tip 120 may be sized to receive a standard needle hub thereon. The needle cannula may be integrally secured within the passage 124 by a chemical adhesive, such as an epoxy, or may be mechanically affixed to the luer tip 120 according to known techniques. The syringe assembly 100 may also include a protective cap (not shown) disposed over the needle cannula to protect the needle cannula prior to use and to prevent accidental needle sticks of persons handling the syringe assembly 100 prior to use. The luer tip 120 may be formed with an external annular ridge 127 to facilitate attachment of a protective cap or a needle hub over the luer tip 120.

A locking mechanism 125 is also disposed within the passage 124 of the luer tip 120 at the proximal end 122 of the luer tip 120. More specifically, the locking mechanism 125 is disposed within a portion of the wall of the syringe barrel 110 that defines the distal end 114 of the syringe barrel 110. For purposes of description and defining the present invention, the luer tip 120 is considered as including the portions of the syringe barrel 110 in which the passage 124 is defined such that the passage 124 is in direct fluid communication with the chamber 112 of the syringe barrel 110. As shown in FIGS. 3-4, the locking mechanism 125 includes a plurality of flexible protrusions 126 disposed about the inside surface 123 of the luer tip 120. These protrusions 126 extend into the passage 124 and are adapted to flex toward the inside surface 123 of the luer tip 120. The protrusions 126 extend into the passage 124 at an angle toward the distal end 121 of the luer tip 120.

Figure 5:
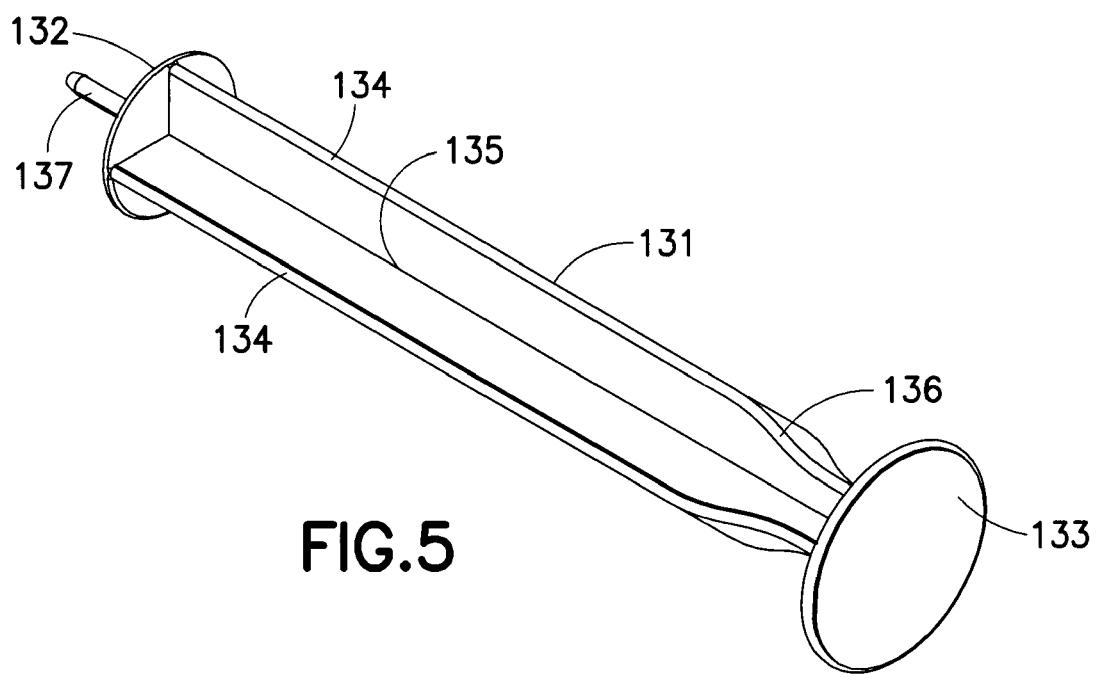
FIG. 5 is a perspective view of a plunger rod and extension of a passive reuse prevention syringe in accordance with an embodiment of the present invention.
Figure 6:
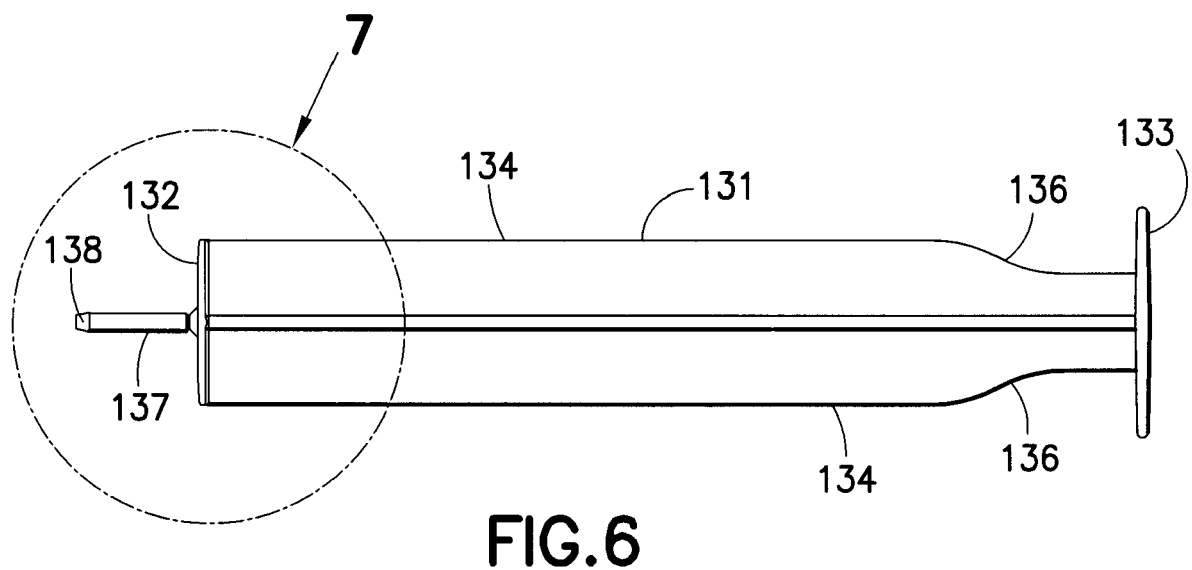
FIG. 6 is a side view of the plunger assembly of FIG. 5.
Figure 7:
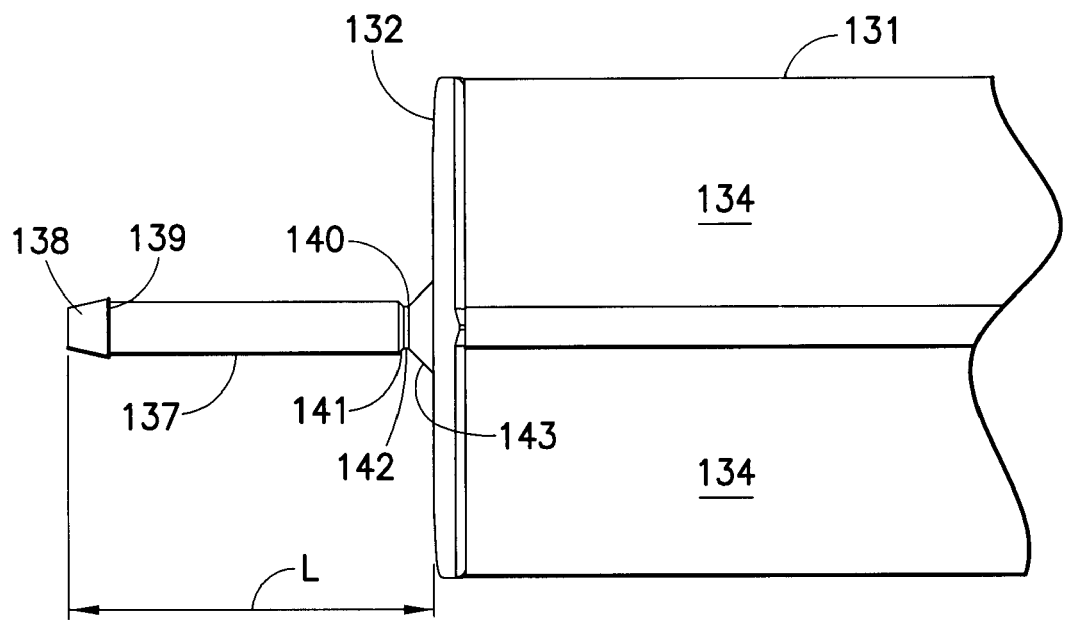
FIG. 7 is an enlarged view of FIG. 6.

Referring to FIGS. 5-13, the syringe assembly 100 also includes a plunger assembly 130 disposed at least partially within the syringe barrel 110 (as shown in FIG. 14). As shown in FIGS. 5-7, the plunger assembly 130 includes an elongate plunger rod 131 that has a distal end surface 132, which is formed as an outwardly extending flange, and another outwardly extending flange 133 at a proximal end thereof. The plunger rod 131 is formed by a plurality of walls 134 that radially extend from a common center portion 135 and extend longitudinally between the distal end surface 132 and the proximal outwardly extending flange 133 of the plunger rod 131. Additionally, the walls 134 may be formed with inward tapering portions 136 proximate to the outwardly extending flange 133 at the proximal end of the plunger rod 131 so as to facilitate gripping of the plunger rod 131. It is to be appreciated that the plunger rod 131 may be formed in any suitable shape so long as the plunger rod 131 substantially conforms to the shape of the inside surface 111 of the syringe barrel 110 such that the plunger rod 131 can be inserted in and withdrawn from the chamber 112 of the syringe barrel 110 without excessive vacillation. To that end, the radially extending walls 134 of the plunger rod may have a width substantially equal to half a width of the chamber 112 of the syringe barrel 110 and the distal end surface 132 also has a width substantially equal to the width of the chamber 112 of the syringe barrel 110.

A cylindrically-shaped extension 137 is integrally formed with the plunger rod 131 and extends distally from the distal end surface 132 of the plunger rod 131. The extension 137 includes a tip 138 formed at the distal end of the extension 137. As shown in FIG. 7, the tip 138 of the extension 137 tapers outwardly from the distal end of the extension 137 toward the distal end surface 132 of the plunger rod 131 so as to have a substantially conical shape. The tip 138 thus forms an abutment surface 139 between the extension 137 and the tip 138 at its widest part, which encircles the extension 137. As shown in FIGS. 5-7, the plunger rod 131 and extension 137 are formed as a single, continuous piece with the plunger rod 131 and the extension 137 being integrally connected by a breakable neck portion 140 extending between the distal end surface 132 of the plunger rod 131 and the proximal end of the extension 137. As shown in FIG. 7, the breakable neck portion 140 has a center portion 142 disposed between the proximal end of the extension 137 and the distal end surface 132 of the plunger rod 131. The breakable neck portion 140 includes inwardly and outwardly tapered portions 141, 143 extending from the proximal end of the extension 137 and the distal end surface 132 of the plunger rod, respectively, so as to have a reduced diameter at the center portion 142. As such, the axial strength of the breakable neck portion 140 is reduced at the center portion 142 and the breakable neck portion 140 is adapted to break upon application of a sufficient axial force to the plunger rod 131 in the proximal direction. It is to be appreciated that the extension 137 and tip 138 can be provided in any suitable shape and configuration. Additionally, the plunger rod 131 and extension 137 may be injection molded from thermoplastic material such as polypropylene, polyethylene, and polystyrene according to techniques known to those of ordinary skill in the art, though it is to be appreciated that the plunger rod 131 and extension 137 may be made from other suitable materials and according to other applicable techniques.

Figure 8:
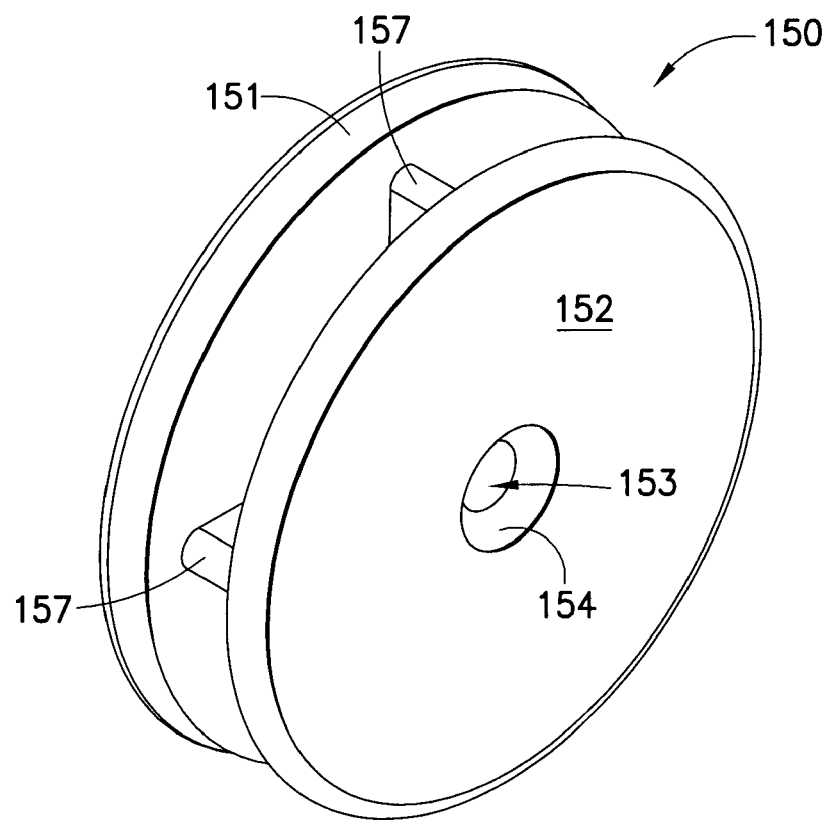
FIG. 8 is a perspective view of a plunger head of a passive reuse prevention syringe in accordance with an embodiment of the present invention.
Figure 10:
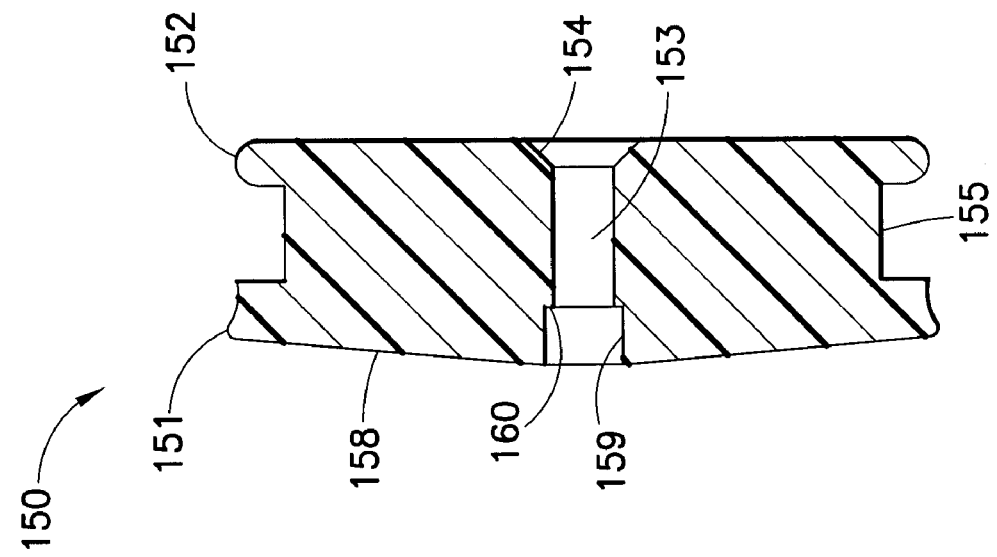
FIG. 10 is a cross-sectional side view of the plunger head of FIG. 8.
Figure 9:
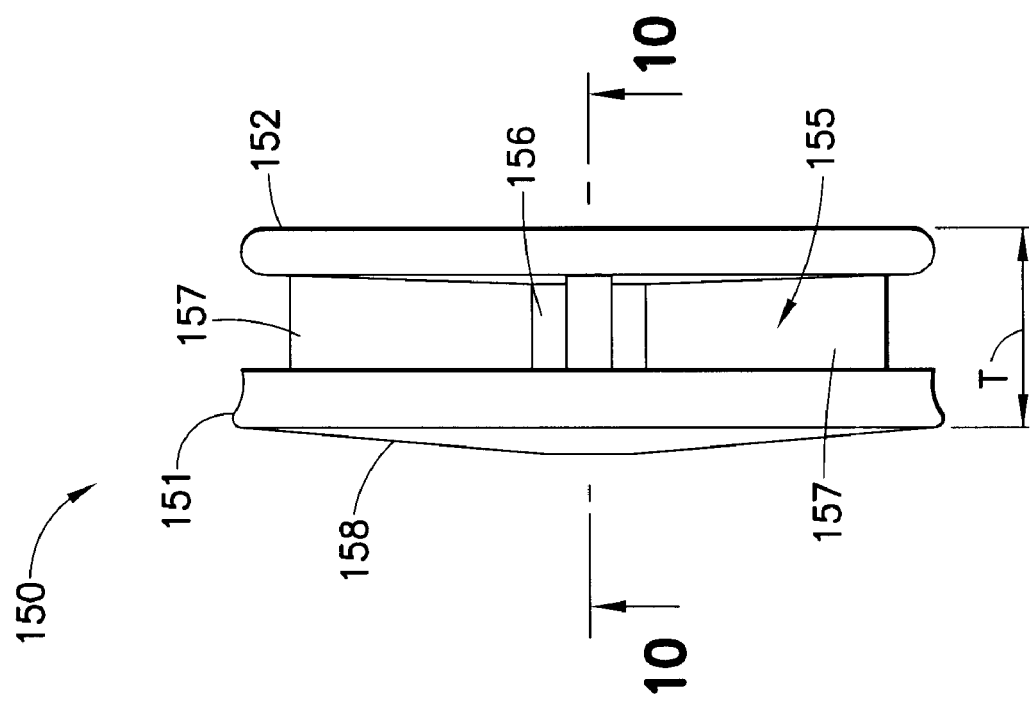
FIG. 9 is a side view of the plunger head of FIG. 8.

With reference to FIGS. 8-10, the plunger assembly 130 also includes a plunger head 150 that is slidably disposed on the extension 137 between the tip 138 of the extension 137 and the distal end surface 132 of the plunger rod 131. The plunger head 150 includes a distal wall 151 and a proximal wall 152. The distal wall 151 has a distal sealing surface 158 of the plunger head 150 defined thereon. As shown in FIGS. 14-19, the distal wall 151 of the plunger head 150 perimetrically engages the inside surface 111 of the syringe barrel 110 so as to seal the chamber 112 of the syringe barrel 110 during use of the syringe assembly 100. The distal and proximal walls 151, 152 of the plunger head 150 are spaced by a central portion 155 of the plunger head 150 that extends between the distal and proximal walls 151, 152 of the plunger head 150. The central portion 155 has a cylindrical core portion 156 and a plurality of equally spaced fin portions 157 extending radially from the cylindrical core portion 156. As shown, there are four equally spaced fin portions 157, though there could be more or less so long as the distal wall 151 of the plunger head 150 is suitably supported against canting, thus breaking a sealing engagement between the distal wall 151 and the inside surface 111 of the syringe barrel 110 during use. The distal wall 151, proximal wall 152, and cylindrical core portion 156 define a hole 153 extending through the plunger head 150. The hole 153 is sized to receive the extension 137 therein. As shown in FIG. 10, the hole 153 includes a proximal substantially conical portion 154 in the proximal wall 152 of the plunger head 150 that is shaped to receive the tip 138 of the extension 137 and to mate with the outwardly tapering portion 143 of the breakable neck portion 140 extending from the distal end surface 132 of the plunger rod 131. The hole 153 also includes a distal enlarged diameter portion 159 in the distal wall 151 of the plunger head 150 that is shaped to mate with the tip 138 of the extension 137. The enlarged diameter portion 159 defines an interior abutment surface 160 within the plunger head 150 that engages with the abutment surface 139 at the tip 138 of the extension 137. With further reference to FIGS. 13-19, it is to be appreciated that when the extension 137 is received within the hole 153, the cylindrical core portion 156 sealingly engages extension 137 at the inner diameter of the cylindrical core portion 156 such that fluid cannot pass through the hole 153 during use of the syringe assembly 100.

The plunger head 150 may be integrally molded from either a soft plastic material, such as polyurethane, or alternatively may be formed from a rubber or elastomeric material depending upon choice. Such versatility and interchangeability within the syringe assembly 100 is advantageous because all plastic components can be used in markets where cost is extremely important and an elastomeric plunger head 150 can be used in markets with a strong preference for such components. It is to be appreciated that the plunger head can be formed in different shapes and according to other techniques known to be suitable to those of ordinary skill in the art.

Figure 11:
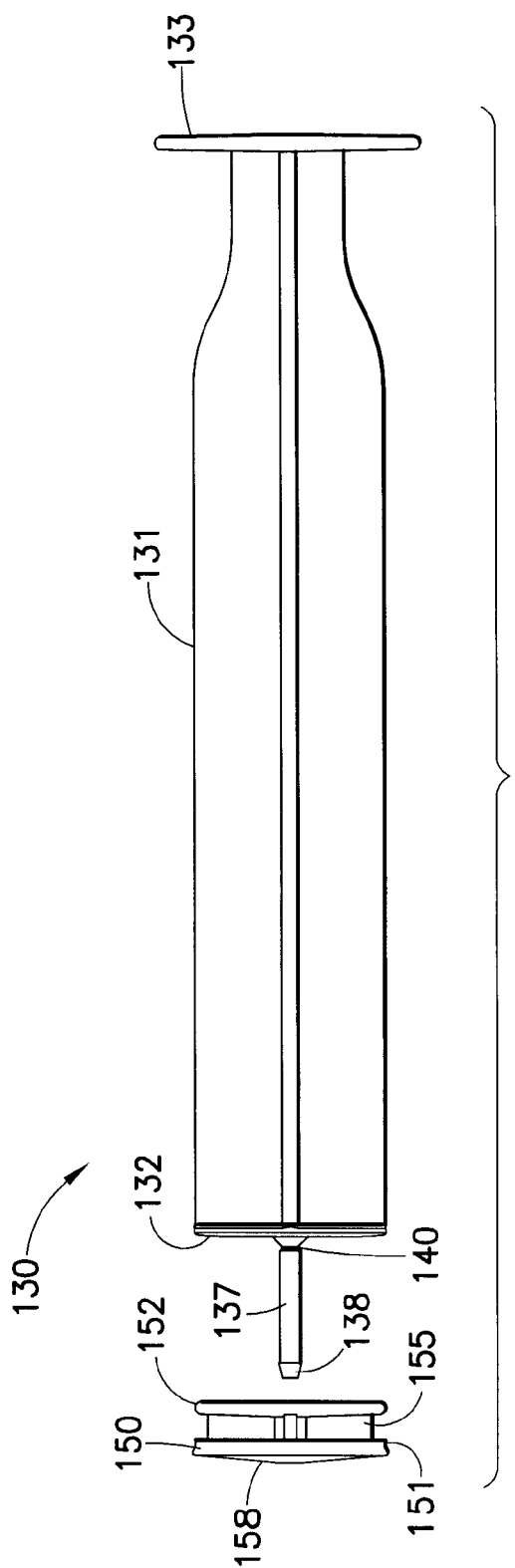
FIG. 11 is a side view of a plunger assembly of a passive reuse prevention syringe in accordance with an embodiment of the present invention.
Figure 12:
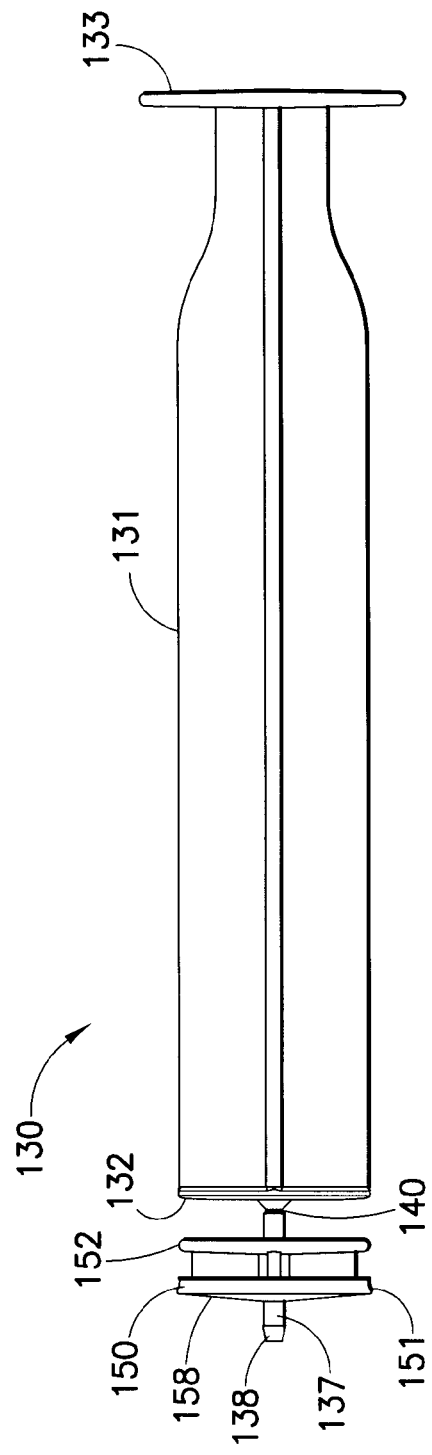
FIG. 12 is a side view of the plunger assembly of FIG. 11 with the plunger head disposed on the extension.

As shown in FIGS. 11-13, the plunger assembly 130 is made up of the integrally formed plunger rod 131 and extension 137 with the plunger head 150 being slidably disposed on the extension 137. The plunger head 150 is placed over the extension 137, which is received within the hole 153 at the proximal substantially conical portion 154 of the hole 153 such that the proximal wall 152 of the plunger head 150 is disposed toward the distal end surface 132 of the plunger rod 131. The extension 137 has a length L (shown in FIG. 7) extending from the distal end surface 132 of the plunger rod 131 to the tip 138 of the extension 137, which is greater than a thickness T of the plunger head 150 (shown in FIG. 9) such that the plunger head 150 is able to slide along the extension 137 from the tip 138 of the extension 137 to the distal end surface 132 of the plunger rod 131.

Referring to FIGS. 14-19, operation of the syringe assembly 100 according to an embodiment of the present invention will now be described in detail. As shown in FIG. 14, at an initial or packaged state of the syringe assembly 100, the plunger rod 131 is disposed at least partially within the chamber 112 of the syringe barrel 110 such that the plunger head 150 is situated proximate to the distal end 114 of the syringe barrel 110. The extension 137 extends through the plunger head 150 such that the tip 138 is situated proximate to the locking mechanism 125 within the luer tip 120. The plunger rod 131 is then partially withdrawn from the syringe barrel 110 in the proximal direction. As this occurs, the plunger head 150 slides with respect to the extension such that the tip 138 of the extension 137 becomes engaged in the distal enlarged diameter portion 159 of the hole 153 extending through the plunger head such that interior abutment surface 160 of the plunger head 150 engages with the abutment surface of the tip 138 of the plunger head 150 and the plunger head 150 is drawn proximally by the plunger rod 131 so as to aspirate the chamber 112 of the syringe barrel 110, as shown in FIG. 15. Pushing the plunger assembly 130 distally when in the packaged state could result in premature locking of the syringe assembly 100.

Once the desired aspiration of the chamber 112 of the syringe barrel 110 is completed, the plunger rod 131 is advanced within the chamber 112 of the syringe barrel 110. As shown in FIG. 16, as the plunger rod 131 is advanced, the plunger head 150 slides with respect to the extension 137 until the proximal wall 152 of the plunger head 150 engages the distal end surface 132 of plunger rod 131 and the proximal substantially conical portion 154 of the hole 153 extends over the inward tapering portion 141 of the breakable neck portion 140 extending from the distal end surface 132 of plunger rod 131. The plunger assembly 130 is then further advanced within the chamber 112 of the syringe barrel 110 with the plunger head 150 being pushed through the chamber 112 by the distal end surface 132 of the plunger rod 131 so as to inject the contents of the chamber 112 to a patient. Thus, it is to be appreciated that a force necessary to advance the plunger rod 131 relative to the plunger head 150 during the injection cycle between aspiration and injection is less than a force necessary to sustain injection of the contents of the chamber 112 of the syringe barrel 110. By providing a plunger assembly 130 with a slidable plunger head 150, the plunger head 150 can be initially packaged in a bottomed out condition, i.e., abutting or adjacent to the distal end 114 of the syringe barrel 110 and the passage 124 of the luer tip 120. This results in less air being drawn into the chamber 112 of the syringe barrel 110 during aspiration and prior to injection.

As shown in FIG. 17, as the plunger assembly 130 is advanced within the chamber 112 of the syringe barrel 110, the tip 138 of the extension 137 extends into the passage 124 of the luer tip 120 past the locking mechanism 125. As the tip 138 of the extension 137 passes through the locking mechanism 125, the protrusions 126 engage the tip 138 and flex toward the inside surface 123 of the luer tip 120 and allow the tip 138 to pass between them. As shown in FIG. 18, the injection cycle continues until the distal wall 151 of the plunger head 150 comes into engagement with the distal end 114 of the syringe barrel 110 with the extension 137 extending into the passage 124 of the luer tip 120.

If a person attempts to withdraw the plunger assembly 130 from the chamber 112 of the syringe barrel 110 after completion of the injection cycle by pulling on the plunger rod 131, the extension 137 and the tip 138 of the extension 137 will be retained in a locked position at least partially within the passage 124 of the luer tip 120 by an engagement between the tip 138 of the extension 137 at the abutment surface 139 and the flexible protrusions 126 of the locking mechanism 125 such that removal of the tip 138 of the extension 137 from the passage 124 of the luer tip 120 is prevented.

Figure 19:
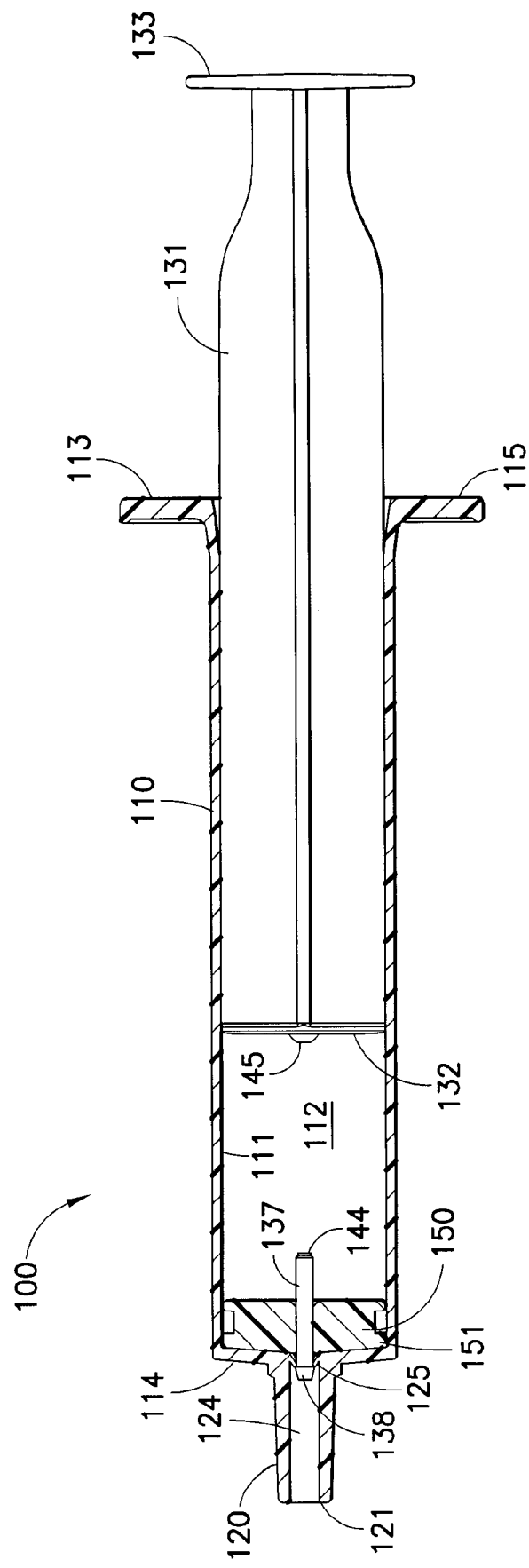
FIG. 19 is a partial cross-sectional side view of the passive reuse prevention syringe of FIG. 14 with the locked plunger being broken into two pieces.

With reference to FIG. 19, once full injection of the contents of the chamber 112 of the syringe barrel 110 is completed and the tip 138 of the extension 137 is retained in the locked position within the passage 124 of the luer tip 120, continued pulling on the plunger rod 131 in a proximal direction will result in the breakable neck portion 140 of the extension 137 breaking apart at or near the center portion 142 such that the tip 138 of the extension 137 remains in the locked position and the plunger head 150 remains at the distal end 114 of the syringe barrel 110 due to engagement between the tip 138 of the extension 137 and the locking mechanism 125 while the plunger rod 131 is separated from the extension 137 and may be removed from the chamber 112 of the syringe barrel 110. Nub portions 144, 145 remain on the proximal end of the extension 137 and the distal end surface 132 of the plunger rod 131, respectively, after the breakable neck portion 140 has been broken. The extension 137 and plunger head 150 remain in the passage 124 and chamber 112, as described, thus blocking the chamber 112 of the syringe barrel 110 and sealing the passage 124 of the luer tip 120 and rendering the syringe assembly 100 completely disabled.

Thus, reuse of the syringe assembly 100 after full injection and disposal of the extension 137 of the plunger assembly 130 in a locked position within the passage 124 of the luer tip 120 is prevented as the plunger assembly 130 will be broken into two pieces if a person attempts to withdraw the plunger assembly 130 from the syringe barrel 110 or re-aspirate the chamber 112 of the syringe barrel 110. It is to be appreciated that the breakable neck portion 140 may be structured to break upon application of any force to the plunger rod 131 by a user, though the breaking force required to break the breakable neck portion 140 and separate the plunger rod 131 from the extension 137 should be greater than a force necessary to at least partially aspirate the chamber 112 of the syringe barrel 110 but less than a force necessary to withdraw the tip 138 of the extension 137 of the plunger assembly 130 past the locking mechanism 125 of the luer tip 120.

Referring to FIGS. 20-34, a syringe assembly 200 is shown according to an embodiment of the present invention. As shown in FIG. 20, the syringe assembly 200 includes a syringe barrel 210, a hub 230 having a needle cannula 201 extending therefrom, and a plunger assembly 250 disposed at least partially within the syringe barrel 210. As shown in FIGS. 21-22, the syringe barrel 210 has an outlet 220 extending from a distal end 212 of the syringe barrel 210. The syringe barrel 210 also has an open proximal end 211 opposite to the distal end 212 of the syringe barrel 210. The outlet 220 has a proximal end 222 attached to the distal end 212 of the syringe barrel 210 and a distal end 221 opposite to the proximal end 222 of the outlet 220. As shown, the syringe barrel 210 and outlet 220 are integrally formed and may have a cylindrical or substantially cylindrical shape, and may include an outwardly extending flange 213 at the open proximal end 211 of the barrel 210, though it is to be appreciated that the syringe barrel 210 and outlet 220 may be formed in any suitable shape or formed separately and attached. Additionally, the syringe barrel 210 and outlet 220 may be injection molded from thermoplastic material such as polypropylene and polyethylene according to techniques known to those of ordinary skill in the art, though it is to be appreciated that the syringe barrel 210 and outlet 220 may be made from other suitable materials, including glass, and according to other applicable techniques.

As shown in FIGS. 22-23, the syringe barrel 210 has an inside surface 214 that defines a chamber 215. Also, the outlet 220 has an inside surface 223 that defines a passage 224 in fluid communication with the chamber 215 of the syringe barrel 210. The passage 224 of the outlet 220 is sized to accommodate a hub 230 (shown in FIGS. 24-25) thereon. To that end, outlet 220 includes a distal end portion 227 having an increased diameter tapering outwardly in a direction toward the proximal end 222 of the outlet 220 so as to facilitate a mating engagement with the hub 230.

A locking mechanism 225 is disposed within the passage 224 of the outlet 220 at the proximal end 222 of the outlet 220. More specifically, the locking mechanism 225 is disposed within a portion of the wall of the syringe barrel 210 that defines the distal end 212 of the syringe barrel 210. For purposes of description and defining the present invention, the outlet 220 is considered as including the portions of the syringe barrel 210 in which the passage 224 is defined such that the passage 224 is in direct fluid communication with the chamber 215 of the syringe barrel 210. As shown in FIGS. 22-23, the locking mechanism 225 includes a plurality of flexible protrusions 226 disposed about the inside surface 223 of the outlet 220. These protrusions 226 extend into the passage 224 and are adapted to flex toward the inside surface 223 of the outlet 220. The protrusions 226 extend into the passage 224 at an angle toward the distal end 221 of the outlet 220.

Figure 24:
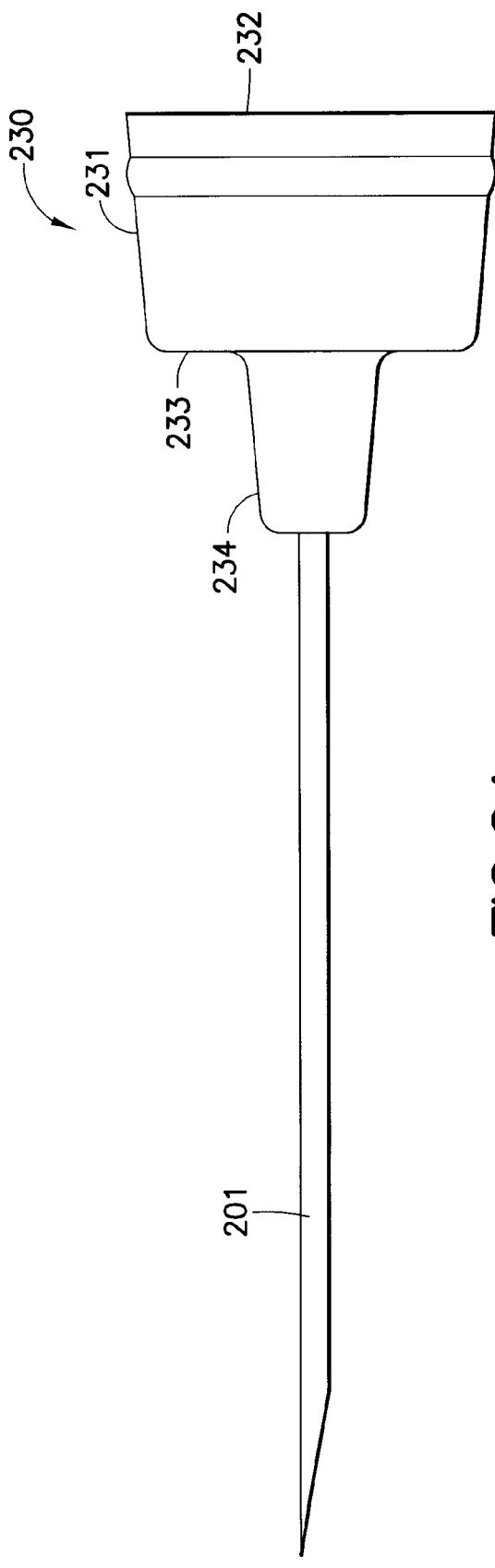
FIG. 24 is a side view of a hub and cannula of the passive reuse prevention syringe of FIG. 20.
Figure 25:
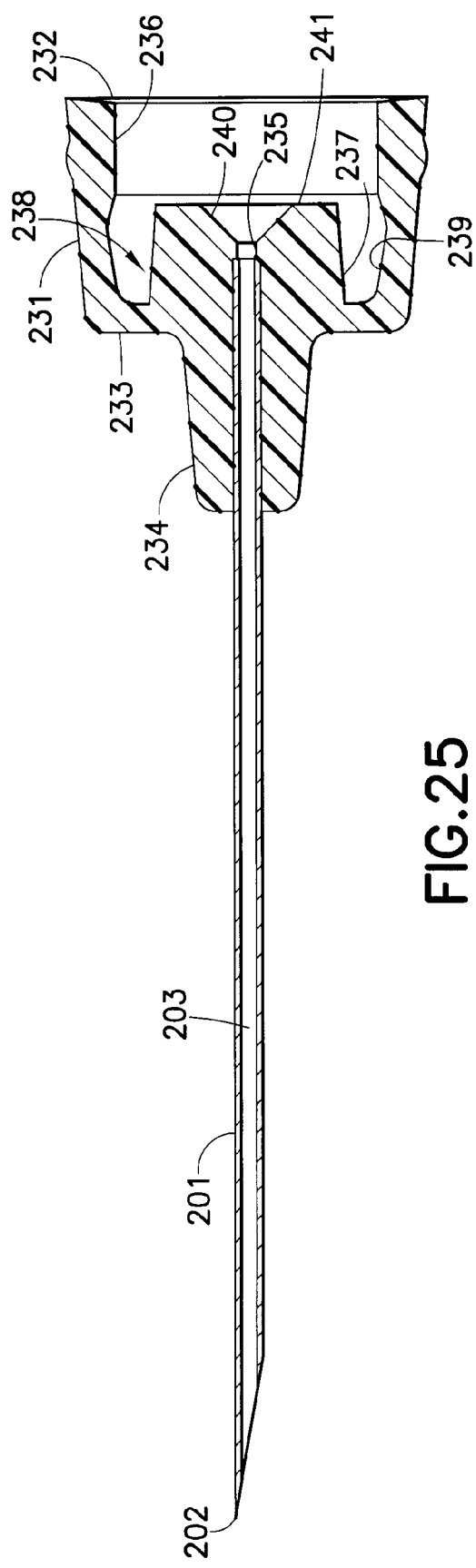
FIG. 25 is a cross-sectional side view of the hub and cannula of FIG. 24.

Referring to FIGS. 24-26, the syringe assembly 200 includes a hub 230 disposed on the outlet 220, which holds a needle cannula 201 therein. The needle cannula 201 includes a pointed tip 202 at a distal end thereof and a hollow passage 203 extending therethrough. The proximal end of the cannula 201 is secured within the hub 230. As shown in FIG. 24, the hub 230 includes a cylindrical skirt portion 231 that has an open proximal end 232 and a distal end 233. A tip 234 extends from the distal end 233 of the cylindrical skirt portion 231. As shown in FIG. 25, the tip 234 includes an orifice 235 extending therethrough that is in fluid communication with an interior 236 of the cylindrical skirt portion 231. The cylindrical skirt portion 231 is disposed on the outlet 220 and forms a mating engagement with the outlet 220 such that the orifice 235 of the hub 230 is in fluid communication with the passage 224 of the outlet 220. The hub 230 also includes a plug portion 237 that extends proximally from the distal end 233 of the cylindrical skirt portion 231 such that an annular recess 238 is formed between the plug portion 237 and cylindrical skirt portion 231. The annular recess 238 has an outwardly tapering surface 239 corresponding to the shape of the distal end portion of the outlet 220. As shown in FIG. 27, the plug portion 237 of the hub 230 extends into the passage 224 of the outlet 220 of the syringe barrel 210 so as to close the passage 224 and cause the distal end portion 227 of the outlet 220 to engage the hub 230 within the annular recess 238 in a secured mating engagement. More particularly, the secured mating engagement between the cylindrical skirt portion 231 of the hub 230 and the outlet 220 may be permanent through the use of an interference fit between the plug portion 237 of the hub 230 and the inside surface 223 of the outlet 220, through deformation of the distal end portion 227 of the outlet 220, through use of a chemical adhesive between the hub 230 and the outlet 220, or by placing the locking mechanism 225 within the hub 230 as opposed to the outlet 220 such that the hub 230 becomes locked on to the outlet 220 of the syringe assembly 200 via engagement with the plunger assembly 250 and cannot be removed by hand. The syringe assembly 200 is packaged with the hub 230 disposed on the outlet 220 and the permanent engagement prevents tampering or reuse of the hub 230 and needle cannula 201 by healthcare workers and potential downstream users.

Figure 33:
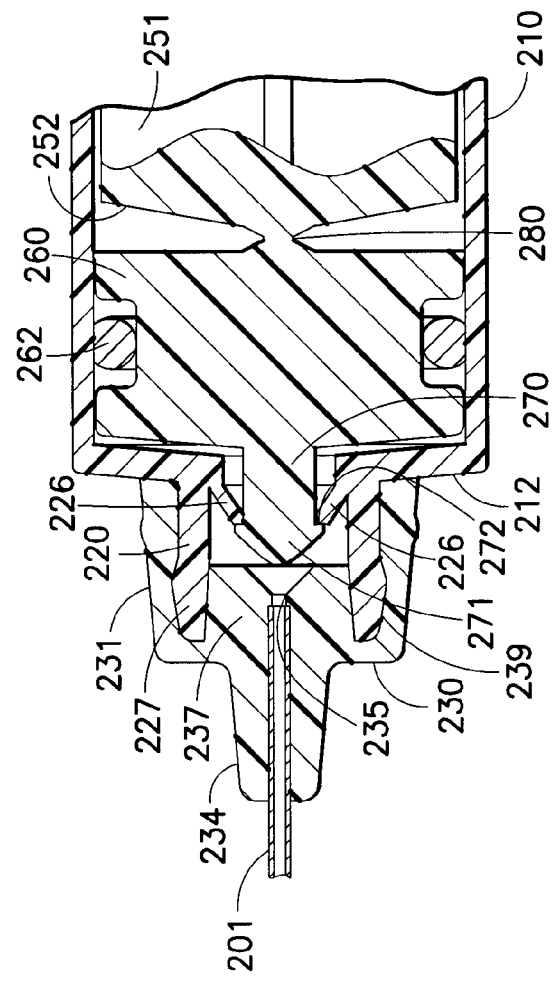
FIG. 33 is an enlarged sectional view of FIG. 32.

As shown in FIG. 25, the orifice 235 of the tip 234 of the hub 230 extends through the plug portion 237 and includes a conical inlet 240 at a proximal surface of the plug 241. The conical inlet 240 is shaped to correspond to a shape of a tip 271 of an extension 270 of the plunger assembly 250 (as shown in FIG. 33). It is to be appreciated that by providing the syringe assembly 200 according to the current embodiment with a separate hub 230 that carries the needle cannula 201, the outlet 220 may be formed larger with a wider passage 224 so as to facilitate easier molding of the syringe barrel 210 and outlet 220 and the formation of the flexible protrusions 226 of the locking mechanism 225.

Also as shown in FIG. 25, the needle cannula 201 may be secured within the orifice 235 of the needle tip 234 and plug portion 237 of the hub 230 by a chemical adhesive, such as epoxy, or may be mechanically affixed to the tip 234 of the hub 230 according to known techniques. For instance, the tip 234 of the hub 230 may be modified to receive a separate needle hub thereon via a standard luer taper fitting or luer lock fitting. The syringe assembly 200 may also include a protective cap (not shown) disposed over the needle cannula 201 to protect the needle cannula 201 prior to use and to prevent accidental needle sticks of persons handling the syringe assembly 200 prior to use. The tip 234 may be formed to facilitate attachment of a protective cap or a standard needle hub over the tip 234.

Figure 28:
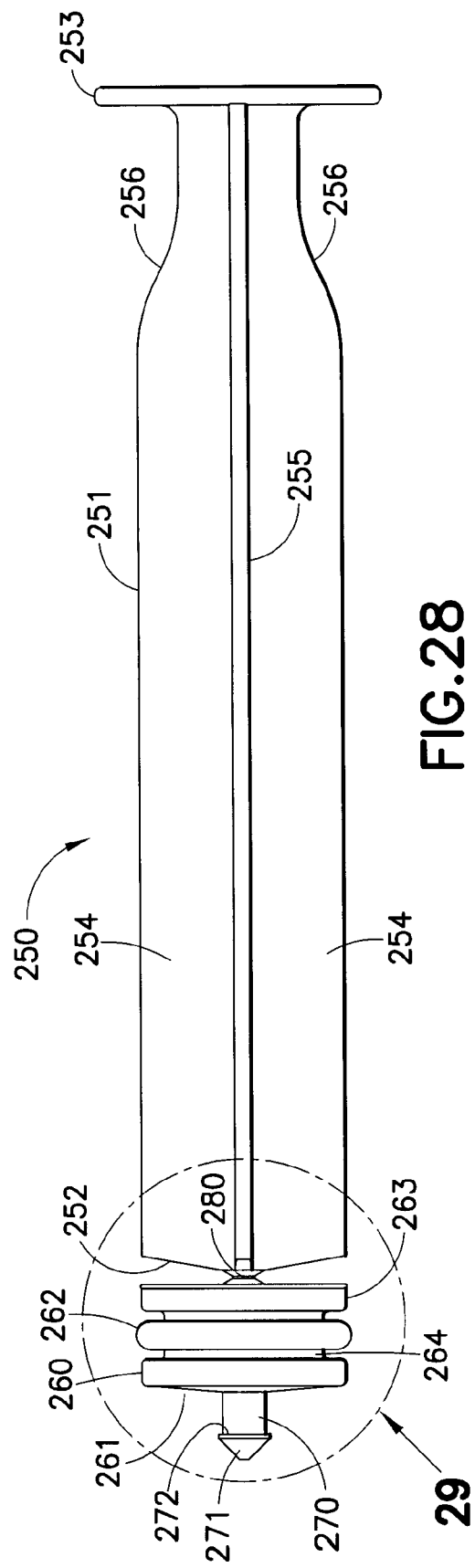
FIG. 28 is a side view of a plunger assembly of the passive reuse prevention syringe of FIG. 20.
Figure 29:
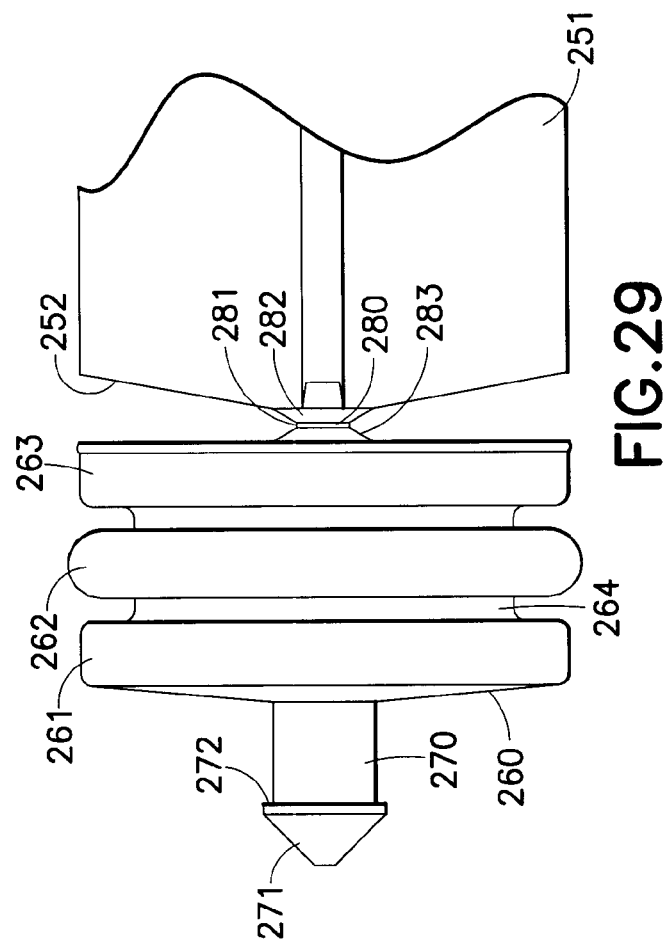
FIG. 29 is an enlarged side view of the plunger assembly of FIG. 28.

Referring to FIGS. 28-29, the syringe assembly 200 also includes a plunger assembly 250 disposed at least partially within the syringe barrel 210 (shown in FIG. 30). The plunger assembly 250 includes an elongate plunger rod 251 that has a distal end surface 252 and an outwardly extending flange 253 at a proximal end thereof. The plunger rod 251 is formed by a plurality of walls 254 that radially extend from a common center portion 255 and extend longitudinally between the distal end surface 252 and the proximal outwardly extending flange 253 of the plunger rod 251. Additionally, the walls 254 may be formed with inward tapering portions 256 proximate to the outwardly extending flange 253 at the proximal end of the plunger rod 251 so as to facilitate gripping of the plunger rod 251. It is to be appreciated that the plunger rod 251 may be formed in any suitable shape so long as the plunger rod 251 substantially conforms to the shape of the inside surface 214 of the syringe barrel 210 such that plunger rod 251 can be inserted in and withdrawn from the chamber 215 of the syringe barrel 210 without excessive vacillation. To that end, the radially extending walls 254 of the plunger rod 251 may have a width substantially equal to half a width of the chamber 215 of the syringe barrel 210.

The plunger assembly 250 also includes a plunger head 260 and extension 270 integrally formed with the plunger rod 251 and connected to the distal end surface 252 of the plunger rod 251. The plunger head 260 includes a distal wall 261 and a proximal wall 263. The distal wall 261 and the proximal wall 263 are spaced by a central portion 264 of the plunger head 260 that extends between the distal 261 and proximal 263 walls and has a diameter less than the diameter of the distal 261 and proximal 263 walls. An elastomeric sealing member or O-ring 262 is disposed on the central portion 264 of the plunger head 260 between the distal 261 and proximal 263 walls. The O-ring 262 engages the inside surface 214 of the syringe barrel 210 about the perimeter of plunger head 260 so as to seal the chamber 215 of the syringe barrel 210 during use of the syringe assembly 200. It is to be appreciated that the plunger head 260 may be formed in any suitable shape and configuration, including an arrangement where the distal wall 261 perimetrically engages the inside surface 214 of the syringe barrel 210 to seal the chamber 215.

A cylindrically-shaped extension 270 is integrally formed with the plunger head 260 and is disposed on the distal wall 261 of the plunger head 260 and extends distally from the distal wall 261. The extension 270 includes a tip 271 formed at the distal end of the extension 270. The tip 271 of the extension 270 tapers outwardly from the distal end of the extension 270 toward the distal wall 261 of the plunger head 260 so as to have a substantially conical shape. The tip 271 thus forms an abutment surface 272 between the extension 270 and the tip 271 at its widest part, which encircles the extension 270. The plunger rod 251, plunger head 260, and extension 270 are formed as a single, continuous piece with the plunger rod 251 and plunger head 260 being integrally connected by a breakable neck portion 280 extending between the distal end surface 252 of the plunger rod 251 and the proximal wall 263 of the plunger head 260. As shown in FIG. 29, the breakable neck portion 280 has a center portion 281 disposed between the proximal wall 263 of the plunger head 260 and the distal end surface 252 of the plunger rod 251. The breakable neck portion 280 includes inwardly tapered portions 282, 283 extending from the distal end surface 252 of the plunger rod 251 and the proximal wall 263 of the plunger head 260, respectively, so as to have a reduced diameter at the center portion 281. As such, the axial strength of the breakable neck portion 280 is reduced at the center portion 281 and the breakable neck portion 280 is adapted to break upon application of a sufficient axial force to the plunger rod 251 in the proximal direction. It is to be appreciated that the extension 270 and tip 271 can be provided in any suitable shape and configuration. The plunger rod 251, plunger head 260, and extension 270 may be injection molded from thermoplastic material such as polypropylene, polyethylene, and polystyrene according to techniques known to those of ordinary skill in the art, though it is to be appreciated that the plunger rod 251, the plunger head 260, and the extension 270 may be made from other suitable materials and according to other applicable techniques. Alternatively, the plunger assembly 250 could be formed such that the plunger head 260 is slidably disposed on the extension 270, as described above with reference to FIGS. 5-18.

Referring to FIGS. 31-34, operation of the syringe assembly 200 according to an embodiment of the present invention will now be described in detail. As shown in FIG. 30, at an initial or packaged state of the syringe assembly 200, the plunger rod 251 is disposed at least partially within the chamber 215 of the syringe barrel 210 such that the plunger head 260 is situated proximate to the distal end 212 of the syringe barrel 210. The extension 270 extends from the distal wall 261 of the plunger head 260 such that the tip 271 is situated proximate to the locking mechanism 225 within the outlet 220. The plunger rod 251 is then partially withdrawn from the syringe barrel 210 in the proximal direction so as to aspirate the chamber 215 of the syringe barrel 210 and fill the syringe, as is shown in FIG. 31. Pushing the plunger assembly 250 distally when in the packaged state could result in premature locking of the syringe assembly 200.

Figure 32:
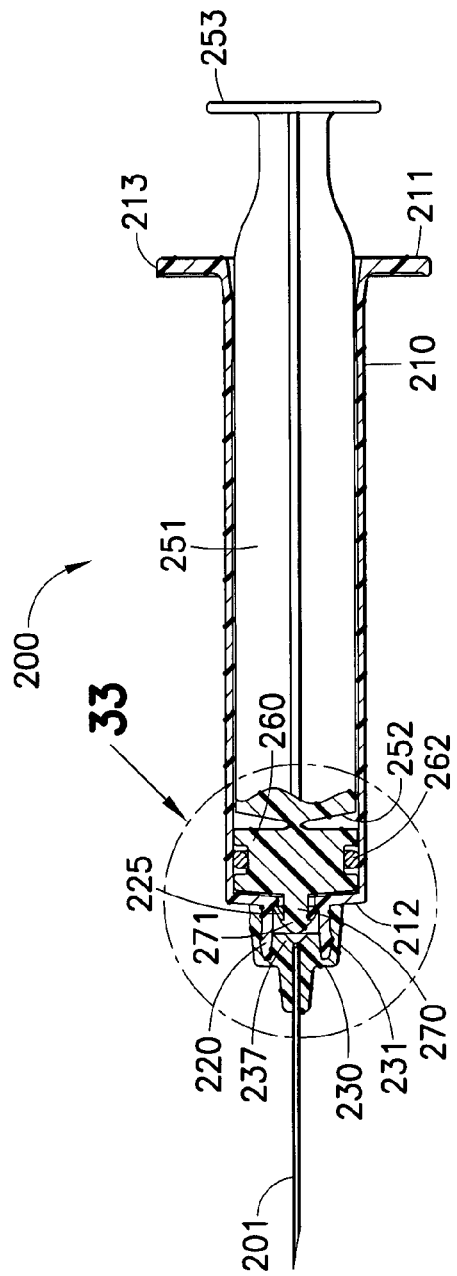
FIG. 32 is a partial cross-sectional side view of the passive reuse prevention syringe of FIG. 20 after injection of the contents of the syringe, and with the extension being situated in a locked position.

Once the desired aspiration of the chamber 215 of the syringe barrel 210 is complete, the plunger rod 251 is advanced within the chamber 215 of the syringe barrel 210 to inject the contents of the syringe barrel 210 to a patient. As shown in FIG. 32, as the plunger assembly 250 is advanced within the chamber 215 of the syringe barrel 210, the tip 271 of the extension 270 extends into the passage 224 of the outlet 220 past the locking mechanism 225. As the tip 271 of the extension 270 passes through the locking mechanism 225, the protrusions 226 engage the tip 271 and flex toward the inside surface 223 of the outlet 220 and allow the tip 271 to pass between them. The injection cycle continues until the distal wall 261 of the plunger head 260 comes into engagement with the distal end 212 of the barrel 210 with the extension 270 extending into the passage 224 of the outlet 220.

As shown in FIG. 33, if a person attempts to withdraw the plunger assembly 250 from the chamber 215 of the syringe barrel 210 after completion of the injection cycle by pulling on the plunger rod 251, the extension 270, and the tip 271 of the extension 270 will be retained in a locked position at least partially within the passage 224 of the outlet 220 by an engagement between the tip 271 of the extension 270 at the abutment surface 272 and the flexible protrusions 226 of the locking mechanism 225 such that removal of the tip 271 of the extension 270 from the passage 224 of the outlet 220 is prevented.

With reference to FIG. 34, once full injection of the contents of the chamber 215 of the syringe barrel 210 is completed and the tip 271 of the extension 270 is retained in the locked position within the passage 224 of the outlet 220, continued pulling on the plunger rod 251 in a proximal direction will result in the breakable neck portion 280 of the plunger assembly 250 breaking apart at or near the center portion 281 such that the tip 271 of the extension 270 remains in the locked position and the plunger head 260 remains at the distal end 212 of the syringe barrel 210 due to engagement between the tip 271 of the extension 270 and the locking mechanism 225 while the plunger rod 251 is separated from the plunger head 260 and may be removed from the chamber 215 of the syringe barrel 210. Nub portions 284, 285 remain on the distal end surface 252 of the plunger rod 251 and the proximal wall 263 of the plunger head 260, respectively, after the breakable neck portion 280 of the plunger assembly 250 has been broken. The extension 270 and plunger head 260 remain in the passage 224 and the chamber 215, as described, thus blocking the chamber 215 of the syringe barrel 210 and sealing the passage 224 of the outlet 220 and rendering the syringe assembly 200 completely disabled.

Thus, reuse of the syringe assembly 200 after full injection and disposal of the extension 270 of the plunger assembly 250 in a locked position within the passage 224 of the outlet 220 is prevented as the plunger assembly 250 will be broken into two pieces if a person attempts to withdraw the plunger assembly 250 from the syringe barrel 210 or re-aspirate the chamber 215 of the syringe barrel 210. It is to be appreciated that the breakable neck portion 280 may be structured to break upon application of any force to the plunger rod 251 by a user, though the breaking force required to break the breakable neck portion 280 and separate the plunger rod 251 from the plunger head 260 should be greater than a force necessary to at least partially aspirate the chamber 215 of the syringe barrel 210 but less than a force necessary to withdraw tip 271 of the extension 270 of the plunger assembly 250 past the locking mechanism 225 of the outlet 220.

Referring to FIGS. 35-43, a syringe assembly 300 is shown according to an embodiment of the present invention. As shown in FIG. 35, the syringe assembly 300 includes a syringe barrel 310, a luer tip 320 extending therefrom, and a plunger assembly 340 disposed at least partially within the syringe barrel 310. The syringe barrel 310 has an open proximal end 311 opposite to the distal end 312 of the syringe barrel 310. The luer tip 320 has a proximal end 322 attached to the distal end 312 of the syringe barrel 310 and a distal end 321 opposite to the proximal end 322 of the luer tip 320. As shown, the syringe barrel 310 and luer tip 320 are integrally formed and may have a cylindrical or substantially cylindrical shape, and may include an outwardly extending flange 313 at the open proximal end 311 of the barrel 310, though it is to be appreciated that the syringe barrel 310 and luer tip 320 may be formed in any suitable shape or formed separately and attached. Additionally, the syringe barrel 310 and luer tip 320 may be injection molded from thermoplastic material such as polypropylene and polyethylene according to techniques known to those of ordinary skill in the art, though it is to be appreciated that the syringe barrel 310 and luer tip 320 may be made from other suitable materials, including glass, and according to other applicable techniques. Further, while the luer tip 320 of the syringe assembly 300 is shown as being concentric with the syringe barrel 310, the syringe assembly 300 could be modified to provide the luer tip 320 in an eccentric location on the distal end 312 of the syringe barrel 310. It is to be appreciated that the term "luer" as used herein is intended to encompass not only those tips that meet the standardized requirements for forming a luer lock connection but any conical or substantially conical tip.

Figure 36:
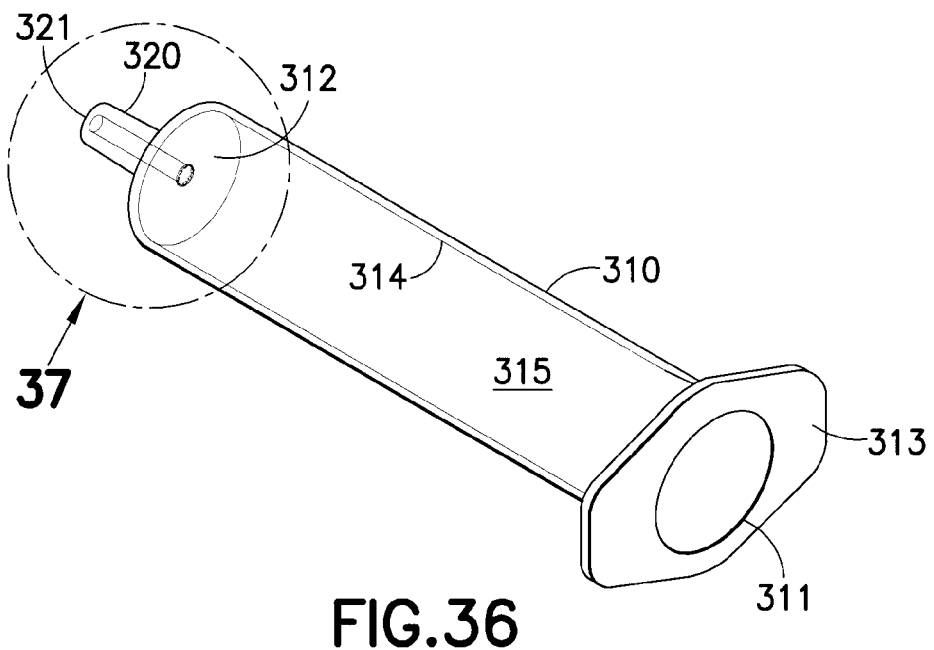
FIG. 36 is a perspective view of a syringe barrel and luer tip of the passive reuse prevention syringe of FIG. 35.
Figure 37:
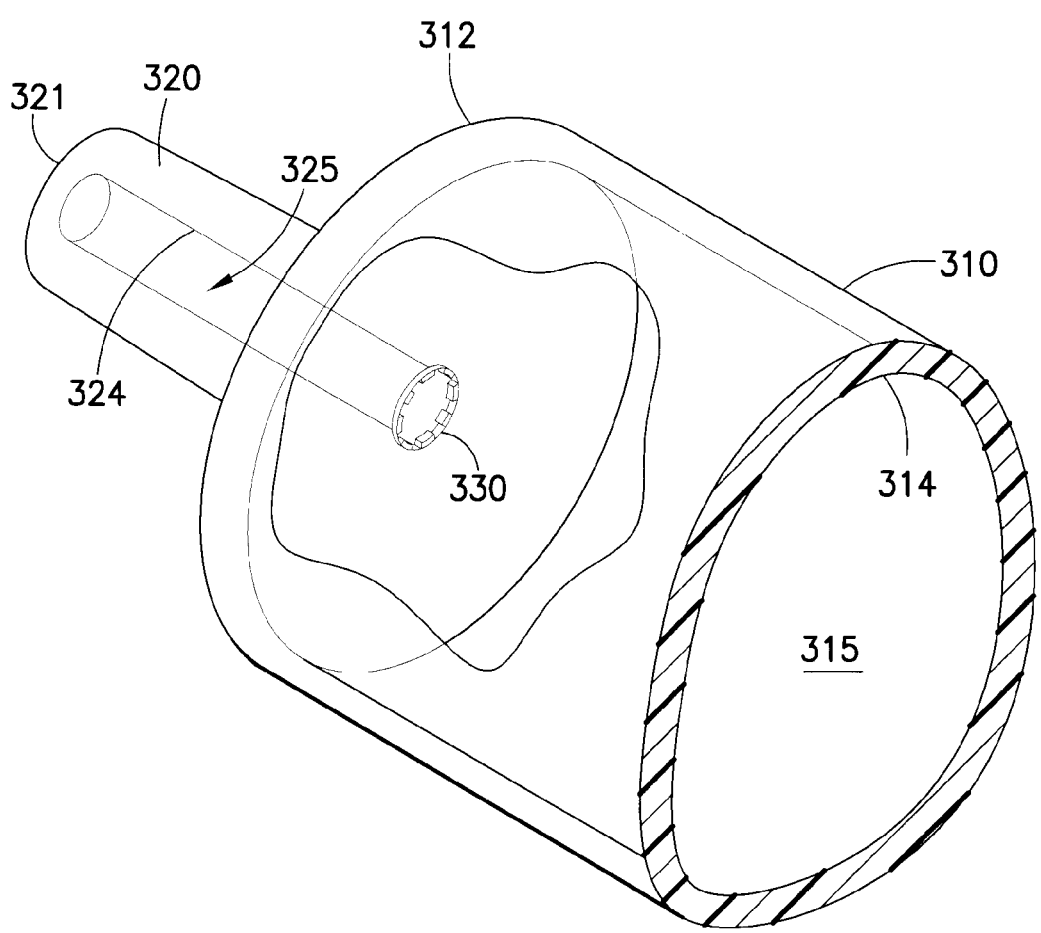
FIG. 37 is an enlarged perspective view of the syringe barrel and luer tip of FIG. 36.

As shown in FIGS. 36-37, the syringe barrel 310 has an inside surface 314 that defines a chamber 315. Also, the luer tip 320 has an inside surface 324 that defines a passage 325 in fluid communication with the chamber 315 of the syringe barrel 310. The passage 325 of the luer tip 320 is sized to receive a needle cannula (such as needle cannula 201, shown in FIG. 20) therein. The needle cannula may be integrally secured within the passage 325 by a chemical adhesive, such as an epoxy, or may be mechanically affixed to the luer tip 320 according to known techniques. The syringe assembly 300 may also include a protective cap (not shown) disposed over the needle cannula to protect the needle cannula prior to use and to prevent accidental needle sticks of a person handling the syringe assembly 300 prior to use. The luer tip 320 may be formed with an external annular ridge 323 to facilitate attachment of a protective cap over the luer tip 320.

Figure 38:
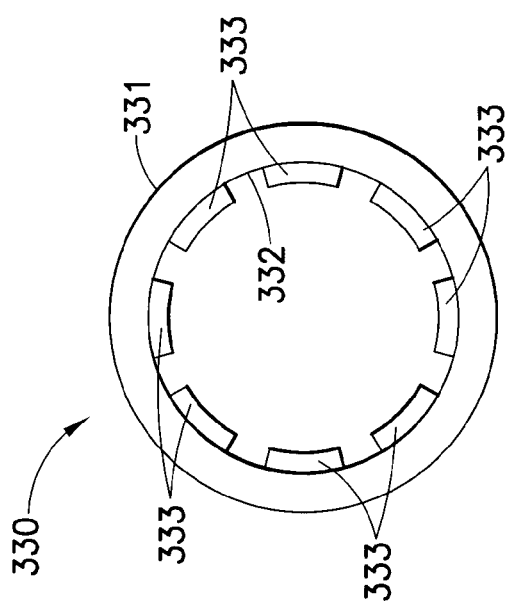
FIG. 38 is a proximal side view of a locking clip of the passive reuse prevention syringe of FIG. 35.

A locking clip 330, which acts as a locking mechanism for the syringe assembly 300, is also disposed within the passage 325 of the luer tip 320 at the proximal end 322 of the luer tip 320. More specifically, the locking clip is disposed within a portion of the wall of the syringe barrel 310 that defines the distal end 312 of the syringe barrel 310. For purposes of description and defining the present invention, the luer tip 320 is considered as including the portions of the syringe barrel 310 in which the passage 325 is defined such that the passage 325 is in direct fluid communication with the chamber 315 of the syringe barrel 310. As shown in FIGS. 37-38, the locking clip 330 includes an outer cylindrical ring 331 having an inner circumferential surface 332 and a plurality of fingers 333 extending from the inner circumferential surface 332. These fingers 333 extend into the passage 325 and are adapted to engage and retain an extension 360 of the plunger assembly 340 via an interference fit between the fingers 333 and the extension (as shown in FIG. 42). The locking clip 330 may be retained within the passage 325 of the luer tip 320 by being snap fit into place in the inside surface 324 of the luer tip 320. It is to be appreciated that the locking clip 330 may be secured within the luer tip 320 by other mechanical engagements, such as by a press fit or by an integral retaining ring or rings being formed on the inside surface 324 of the luer tip 320, or by a chemical adhesive, such as epoxy according to techniques known to those of ordinary skill in the art. The locking clip 330 may be formed from metal, particularly stainless steel, such that the locking clip 330 and fingers 333 are rigid and do not flex when engaging the extension 360. It is to be appreciated that the locking clip 330 may be formed from other metal and non-metal materials according to the current embodiment. It is also to be appreciated that by providing a separate locking clip according to the current embodiment, easier molding of the syringe barrel 310 and luer tip 320 is facilitated as the luer tip 320 does not have to be formed with an integral locking mechanism. Moreover, since the locking clip 330 can be formed to engage the extension 360 of the plunger assembly 340 in an interference fit, the extension 360 does not need to be formed with a widened tip.

Figure 39:
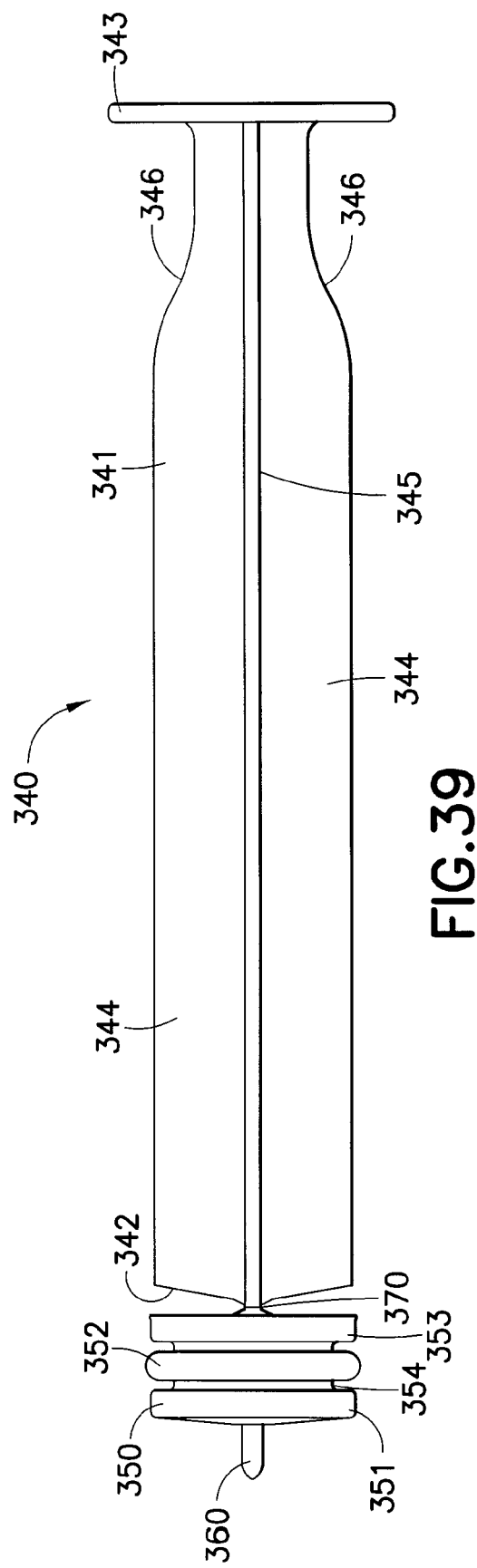
FIG. 39 is a side view of a plunger assembly of the passive reuse prevention syringe of FIG. 35.

Referring to FIG. 39, the syringe assembly 300 also includes a plunger assembly 340 disposed at least partially within the syringe barrel 310 (shown in FIG. 35). The plunger assembly 340 includes an elongate plunger rod 341 that has a distal end surface 342 and an outwardly extending flange 343 at a proximal end thereof. The plunger rod 341 is formed by a plurality of walls 344 that radially extend from a common center portion 345 and extend longitudinally between the distal end surface 342 and the proximal outwardly extending flange 343 of the plunger rod 341. Additionally, the walls 344 may be formed with inward tapering portions 346 proximate to the outwardly extending flange 343 at the proximal end of the plunger rod 341 so as to facilitate gripping of the plunger rod 341. It is to be appreciated that the plunger rod 341 may be formed in any suitable shape so long as the plunger rod 341 substantially conforms to the shape of the inside surface 314 of the syringe barrel 310 such that plunger rod 341 can be inserted in and withdrawn from the chamber 315 of the syringe barrel 310 without excessive vacillation. To that end, the radially extending walls 344 of the plunger rod 341 may have a width substantially equal to half a width of the chamber 315 of the syringe barrel 310.

The plunger assembly 340 also includes a plunger head 350 and extension 360 integrally formed with the plunger rod 341 and connected to the distal end surface 342 of the plunger rod 341. The plunger head 350 includes a distal wall 351 and a proximal wall 353. The distal wall 351 and the proximal wall 353 are spaced by a central portion 354 of the plunger head 350 that extends between the distal 351 and proximal 353 walls and has a diameter less than the diameter of the distal 351 and proximal 353 walls. An elastomeric sealing member or O-ring 352 is disposed on the central portion 354 of the plunger head 350 between the distal 351 and proximal 353 walls. The O-ring 352 engages the inside surface 314 of the syringe barrel 310 about the perimeter of plunger head 350 so as to seal the chamber 315 of the syringe barrel 310 during use of the syringe assembly 300. It is to be appreciated that the plunger head 350 may be formed in any suitable shape and configuration, including an arrangement where the distal wall 351 perimetrically engages the inside surface 314 of the syringe barrel 310 to seal the chamber 315.

A cylindrically shaped extension 360 is integrally formed with the plunger head 350 and is disposed on the distal wall 351 of the plunger head 350 and extends distally from the distal wall 351, though it is to be appreciated that the extension 360 may be provided in any suitable shape and configuration. The plunger rod 341, plunger head 350, and extension 360 are formed as a single, continuous piece with the plunger rod 341 and plunger head 350 being integrally connected by a breakable neck portion 370 extending between the distal end surface 342 of the plunger rod 341 and the proximal wall 353 of the plunger head 350. As shown in FIG. 42, the breakable neck portion 370 has a center portion 371 disposed between the proximal wall 353 of the plunger head 350 and the distal end surface 342 of the plunger rod 341. The breakable neck portion 370 includes inwardly tapered portions 372, 373 extending from the distal end surface 342 of the plunger rod 341 and the proximal wall 353 of the plunger head 350, respectively, so as to have a reduced diameter at the center portion 371. As such, the axial strength of the breakable neck portion 370 is reduced at the center portion 371 and the breakable neck portion 370 is adapted to break upon application of a sufficient axial force to the plunger rod 341 in the proximal direction. The plunger rod 341, plunger head 350, and extension 360 may be injection molded from thermoplastic material such as polypropylene, polyethylene, and polystyrene according to techniques known to those of ordinary skill in the art, though it is to be appreciated that the plunger rod 341, the plunger head 350, and the extension 360 may be made from other suitable materials and according to other applicable techniques. Alternatively, the plunger assembly 340 could be formed such that the plunger head 350 is slidably disposed on the extension 360, as described above with reference to FIGS. 5-18.

Figure 40:
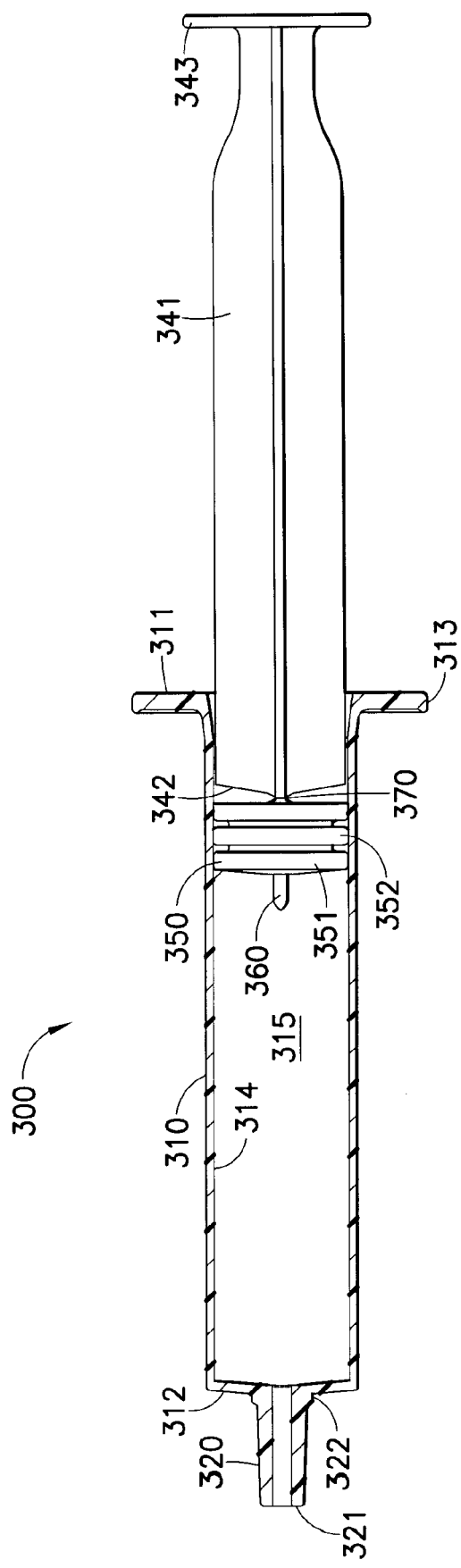
FIG. 40 is a partial cross-sectional side view of the passive reuse prevention syringe of FIG. 35 after aspiration of the syringe.

Referring to FIGS. 35 and 40-43, operation of the syringe assembly 300 according to an embodiment of the present invention will now be described in detail. As shown in FIG. 35, at an initial or packaged state of the syringe assembly 300, the plunger rod 341 is disposed at least partially within the chamber 315 of the syringe barrel 310 such that the plunger head 350 is situated proximate to the distal end 312 of the syringe barrel 310. The extension 360 extends from the distal wall 351 of the plunger head 350 such that the tip 360 is situated proximate to the locking clip 330 within the luer tip 320. The plunger rod 341 is then partially withdrawn from the syringe barrel 310 in the proximal direction so as to aspirate the chamber 315 of the syringe barrel 310 and fill the syringe, as is shown in FIG. 40. Pushing the plunger assembly 340 distally when in the packaged state could result in premature locking of the syringe assembly 300.

Figure 41:
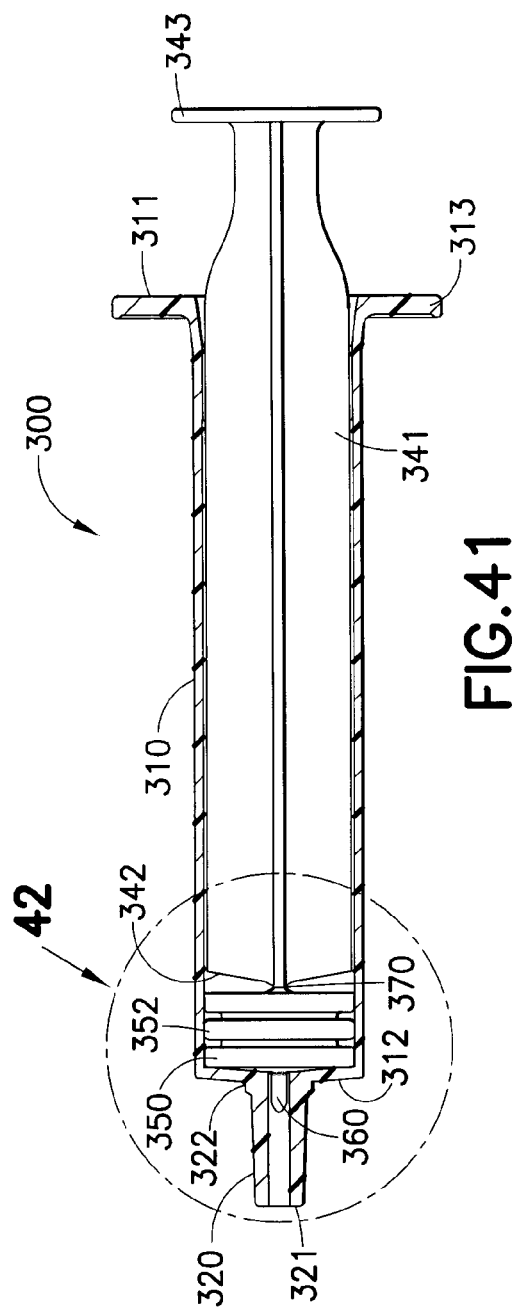
FIG. 41 is a partial cross-sectional side view of the passive reuse prevention syringe of FIG. 35 after injection of the contents of the syringe, and with the extension being situated in a locked position.

Once the desired aspiration of the chamber 315 of the syringe barrel 310 is completed, the plunger rod 341 is advanced within the chamber 315 of the syringe barrel 310 to inject the contents of the syringe barrel 310 to a patient. As shown in FIG. 41, as the plunger assembly 340 is advanced within the chamber 315 of the syringe barrel 310, the extension 360 extends into the passage 325 of the luer tip 320 past the locking clip 330. As the extension 360 passes through the locking clip 330, the fingers 333 of the clip 330 engage the extension 360 in an interference fit, thus restraining the extension 360 from movement in a proximal direction. To that end, the extension 360 may include a rounded or tapered surface at its distal end to facilitate an initial passage of the extension 360 through the locking clip 330, without interference from the fingers 333, as is shown in FIG. 42. The injection cycle continues until the distal wall 351 of the plunger head 350 comes into engagement with the distal end 312 of the barrel 310 with the extension 360 extending into the passage 325 of the luer tip 320.

As shown in FIG. 42, if a person attempts to withdraw the plunger assembly 340 from the chamber 315 of the syringe barrel 310 after completion of the injection cycle by pulling on the plunger rod 341, the extension 360 will be retained in a locked position at least partially within the passage 325 of the luer tip 320 by frictional engagement between the extension 360 and the fingers 333 of the locking clip 330 such that removal of the extension 360 from the passage 325 of the luer tip 320 is prevented. More precisely, the interference fit between the extension 360 and the fingers 333 of the locking clip 330 forms an engagement between the extension 360 and the locking clip 330 that is of sufficient strength such that the breakable neck portion 370 of the plunger assembly 340 will break, as will be described below, before the extension 360 can be removed from engagement with the locking clip 330.

With reference to FIG. 43, once full injection of the contents of the chamber 315 of the syringe barrel 310 is completed and the extension 360 is retained in the locked position within the passage 325 of the luer tip 320, continued pulling on the plunger rod 341 in a proximal direction will result in the breakable neck portion 370 of the plunger assembly 340 breaking apart at or near the center portion 371 such that the extension 360 remains in the locked position and the plunger head 350 remains at the distal end 312 of the syringe barrel 310 due to engagement between the extension 360 and the locking clip 330 while the plunger rod 341 is separated from the plunger head 350 and may be removed from the chamber 315 of the syringe barrel 310. Nub portions 374, 375 remain on the distal end surface 342 of the plunger rod 341 and the proximal wall 353 of the plunger head 350, respectively, after the breakable neck portion 370 of the plunger assembly 340 has been broken. The extension 360 and plunger head 350 remain in the passage 325 and the chamber 315, as described, thus blocking the chamber 315 of the syringe barrel 310 and sealing the passage 325 of the luer tip 320 and rendering the syringe assembly 300 completely disabled.

Thus, reuse of the syringe assembly 300 after full injection and disposal of the extension 360 of the plunger assembly 340 in a locked position within the passage 325 of the luer tip 320 is prevented as the plunger assembly 340 will be broken into two pieces if a person attempts to withdraw the plunger assembly 340 from the syringe barrel 310 or re-aspirate the chamber 315 of the syringe barrel 310. It is to be appreciated that the breakable neck portion 370 may be structured to break upon application of any force to the plunger rod 341 by a user, though the breaking force required to break the breakable neck portion 370 and separate the plunger rod 341 from the plunger head 350 should be greater than a force necessary to at least partially aspirate the chamber 315 of the syringe barrel 310 but less than a force necessary to withdraw the extension 360 of the plunger assembly 340 past the locking clip 330 of the luer tip 320.

So long as the extensions 137, 270, 360 remain unlocked, the syringe assemblies 100, 200, 300 can be used as normal for aspiration and filling of the chambers 112, 215, 315 of the syringe barrels 110, 210, 310 with a medicine or vaccine from a vial or other fluid source and then a patient may be injected with the medicine or vaccine via the needle cannula. Alternatively, the syringe assemblies 100, 200, 300 can be used as normal for the re-constitution of dry drugs. Because the plunger assemblies 130, 250, 340 remain unlocked prior to full injection of the contents of the chambers 112, 215, 315 of the syringe barrels 110, 210, 310, the syringe assemblies 100, 200, 300 allow for variable dosing since the chambers 112, 215, 315 of the syringe barrels 110, 210, 310 can be aspirated to hold varying volumes and their contents can be partially injected without locking the extensions 137, 270, 360. Alternatively, the syringe assemblies 100, 200, 300 can be adapted to provide only fixed doses.

It is to be appreciated that the locking and reuse prevent mechanisms of the present invention are passive mechanisms in that they allow the syringe assemblies 100, 200, 300 to be used as a normal, traditional syringe without automatically locking or preventing reuse but will become locked and disabled by the user through normal operation of the syringe assemblies 100, 200, 300 and full injection of the contents of the syringe assemblies 100, 200, 300. Typically, the extensions 137, 270, 360 will become locked in the luer tips/outlets 120, 220, 320 and the syringe assemblies 100, 200, 300 will be disabled without the user realizing that the locking mechanisms/locking clips 125, 225, 330 has been actuated. Thus a user of the syringe assemblies 100, 200, 300 passively locks and disables the syringe assemblies 100, 200, 300 and the locking mechanisms/locking clips 125, 225, 330 will disable the syringe assemblies 100, 200, 300 after the syringe assemblies 100, 200, 300 have bottomed out upon full injection of the contents of the syringe assemblies 100, 200, 300 without an affirmative action by the user to disable the syringe assemblies 100, 200, 300.

While several embodiments of a passive reuse prevention syringe that uses a retaining ring lock and method were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A syringe assembly, comprising:
    a syringe barrel having an inside surface defining a chamber, an open proximal end, and a distal end;
    a substantially conical tip disposed on the distal end of the barrel, the substantially conical tip having an inside surface defining a passage in fluid communication with the chamber and a locking mechanism disposed within the passage; and
    a plunger assembly disposed at least partially within the syringe barrel, the plunger assembly comprising an elongate plunger rod, an extension disposed on the plunger rod and having a tip on a distal end thereof, and a plunger head slidably disposed on the extension between the tip of the extension and the plunger rod,
    wherein during an injection cycle the plunger head slides with respect to the extension and the plunger rod such that the plunger head engages the tip of the extension during aspiration and engages the plunger rod during injection,
    wherein after completion of the injection cycle, the tip of the extension extends into the passage in the substantially conical tip and engages the locking mechanism so as to prevent removal of the tip of the extension from the substantially conical tip, and
    wherein the locking mechanism comprises a plurality of flexible protrusions disposed about an inside surface of the substantially conical tip and extending into the passage.

2. The syringe assembly according to claim 1, wherein the flexible protrusions are adapted to flex toward the inside surface of the substantially conical tip so as to allow the tip of the extension to pass between them.

3. The syringe assembly according to claim 1, wherein the tip of the extension tapers outwardly from the distal end of the extension so as to form an abutment surface between the extension and the tip at a widest part of the tip, the tip of the extension being engaged by the locking mechanism at the abutment surface.

4. The syringe assembly according to claim 1, wherein the plunger head further comprises:
    a distal wall, the distal wall having a distal sealing surface defined thereon;
    a proximal wall, spaced from the distal wall; and
    a central portion extending between the distal wall and the proximal wall, the central portion having a cylindrical core portion and a plurality of spaced fin portions extending radially from the cylindrical core portion,
    wherein the distal wall, the proximal wall, and the cylindrical core portion of the central portion define a hole extending through the plunger head, the extension being received within the hole, and
    wherein the distal wall of the plunger head perimetrically engages the inner surface of the barrel so as to seal the chamber of the barrel.

5. The syringe assembly according to claim 1, wherein a force necessary to advance the plunger rod relative to the plunger head during the injection cycle between aspiration and injection is less than a force necessary to sustain injection.

6. The syringe assembly according to claim 1, wherein the extension includes a breakable neck portion proximate to the plunger rod, the breakable neck portion being adapted to break upon application of a force to the plunger rod that is greater than a force necessary to at least partially aspirate the syringe, and less than a force necessary to withdraw the tip of the extension of the plunger assembly past the locking mechanism of the substantially conical tip.

7. A syringe assembly, comprising:
    a syringe barrel having an inside surface defining a chamber, an open proximal end, and a distal end;
    a syringe outlet disposed on the distal end of the barrel, the outlet having a cylindrical shape with an outwardly tapering distal end portion, an inside surface defining a passage in fluid communication with the chamber, and a locking mechanism disposed within the passage;

a hub comprising a cylindrical skirt portion having an open proximal end and a distal end; and a plunger assembly disposed at least partially within the syringe barrel, the plunger assembly comprising an elongate plunger rod, a plunger head connected to the plunger rod, the plunger head including a sealing member disposed thereon, and an extension, the extension including a tip on a distal end thereof, wherein the cylindrical skirt portion of the hub is disposed on the outlet and forms a mating engagement with the outlet, wherein the locking mechanism is adapted to engage and retain the tip of the extension of the plunger assembly in a locked position at least partially within the passage of the outlet, and wherein the locking mechanism comprises a plurality of flexible protrusions disposed about the inside surface of the outlet and extending into the passage and the flexible protrusions are disposed within the outlet proximally of the distal end portion of the outlet.

8. The syringe assembly according to claim 7, wherein the plunger head is slidably disposed on the extension.

9. The syringe assembly according to claim 7, wherein the flexible protrusions are adapted to flex toward the inside surface of the outlet so as to allow the tip of the extension to pass between them.

10. The syringe assembly according to claim 7, wherein the hub further comprises a tip extending from the distal end of the cylindrical skirt portion, the tip of the hub having an orifice extending therethrough in fluid communication with an interior of the cylindrical skirt portion such that the orifice is in fluid communication with the passage of the outlet, and a plug portion extending proximally within the cylindrical skirt portion from the distal end of the cylindrical skirt portion so as to form an annular recess between the plug portion and the cylindrical skirt portion, the annular recess being shaped to correspond to the distal end portion of the outlet and the orifice of the tip of the hub extending through the plug portion, and the plug portion of the hub extends into the passage of the outlet of the syringe so as to close the passage and to cause the distal end portion of the outlet to engage the hub within the annular recess in a secured mating engagement.

11. The syringe assembly according to claim 7, wherein the tip of the extension tapers outwardly from the distal end of the extension so as to form an abutment surface between the extension and the tip at a widest part of the tip, the tip of the extension being engaged by the locking mechanism at the abutment surface.

12. The syringe assembly according to claim 7, wherein the plunger head further comprises:
a distal wall;
a proximal wall, spaced from the distal wall; and
a central portion extending between the distal wall and the proximal wall, the central portion having a diameter less than a diameter of the distal and proximal walls,
wherein the sealing member comprises an O-ring disposed around the central portion of the plunger head, the O-ring engaging the inside surface of the barrel so as to seal the chamber.

13. The syringe assembly according to claim 7, wherein the plunger head is connected to the plunger rod by a breakable neck portion, the breakable neck portion being adapted to break upon application of a force to the plunger rod that is greater than a force necessary to at least partially aspirate the syringe, and less than a force necessary to withdraw the tip of the extension of the plunger assembly past the locking mechanism of the outlet.

14. A syringe assembly comprising:
a syringe barrel having an inside surface defining a chamber, an open proximal end, and a distal end;
a substantially conical tip disposed on the distal end of the barrel, the substantially conical tip having an inside surface defining a passage in fluid communication with the chamber and a locking clip disposed within the passage; and
a plunger assembly disposed at least partially within the syringe barrel, the plunger assembly comprising an elongate plunger rod and a plunger head connected to the plunger rod, the plunger head having a sealing member disposed thereon, and an extension,
wherein the locking clip is adapted to engage and retain the extension of the plunger assembly in a locked position at least partially within the passage of the substantially conical tip, and
wherein the locking clip comprises an outer cylindrical ring having an inner circumferential surface and a plurality of rigid fingers extending from the inner circumferential surface into the passage of the substantially conical tip, the fingers being adapted to engage and retain the extension of the plunger assembly via an interference fit.

15. The syringe assembly according to claim 14, wherein the plunger head is slidably disposed on the extension.

16. The syringe assembly according to claim 14, wherein the locking clip is disposed within the substantially conical tip at a proximal end of the substantially conical tip.

17. The syringe assembly according to claim 14, wherein the plunger head further comprises:
a distal wall;
a proximal wall, spaced from the distal wall; and
a central portion extending between the distal wall and the proximal wall, the central portion having a diameter less than a diameter of the distal and proximal walls,
wherein the sealing member comprises an O-ring disposed around the central portion of the plunger head, the O-ring engaging the inside surface of the barrel so as to seal the chamber.

18. The syringe assembly according to claim 14, wherein the plunger head is connected to the plunger rod by a breakable neck portion, the breakable neck portion being adapted to break upon application of a force to the plunger rod that is greater than a force necessary to at least partially aspirate the syringe, and less than a force necessary to withdraw the extension of the plunger assembly past the locking clip of the substantially conical tip.

19. The syringe assembly according to claim 14, wherein the locking clip is made from metal.

20. A syringe assembly, comprising:
a syringe barrel having an inside surface defining a chamber, an open proximal end, and a distal end;
a syringe outlet disposed on the distal end of the barrel, the outlet having a cylindrical shape with an outwardly tapering distal end portion, an inside surface defining a passage in fluid communication with the chamber, and a locking mechanism disposed within the passage;
a hub comprising a cylindrical skirt portion having an open proximal end and a distal end; and
a plunger assembly disposed at least partially within the syringe barrel, the plunger assembly comprising an elongate plunger rod, a plunger head connected to the plunger rod, the plunger head including a sealing member disposed thereon, and an extension, the extension including a tip on a distal end thereof, wherein the cylindrical skirt portion of the hub is disposed on the outlet and forms a mating engagement with the outlet, wherein the locking mechanism is adapted to engage and retain the tip of the extension of the plunger assembly in a locked position at least partially within the passage of the outlet, wherein the hub further comprises a tip extending from the distal end of the cylindrical skirt portion, the tip of the hub having an orifice extending therethrough in fluid communication with an interior of the cylindrical skirt portion such that the orifice is in fluid communication with the passage of the outlet, and a plug portion extending proximally within the interior of the cylindrical skirt portion from the distal end of the cylindrical skirt portion so as to form an annular recess defined within the interior of the cylindrical skirt portion between the plug portion and the cylindrical skirt portion, the annular recess being shaped to correspond to the distal end portion of the outlet and the orifice of the tip of the hub extending through the plug portion, and wherein the plug portion of the hub extends into the passage of the outlet of the syringe so as to close the passage and to cause the distal end portion of the outlet to engage the hub within the annular recess in a secured mating engagement.

21. A syringe assembly, comprising:

a syringe barrel having an inside surface defining a chamber, an open proximal end, and a distal end;

a syringe outlet disposed on the distal end of the barrel, the outlet having a cylindrical shape with an outwardly tapering distal end portion, an inside surface defining a passage in fluid communication with the chamber, and a locking mechanism disposed within the passage;

a hub comprising a cylindrical skirt portion having an open proximal end and a distal end; and a plunger assembly disposed at least partially within the syringe barrel, the plunger assembly comprising an elongate plunger rod, a plunger head connected to the plunger rod, the plunger head including a sealing member disposed thereon, and an extension, the extension including a tip on a distal end thereof, wherein the cylindrical skirt portion of the hub is disposed on the outlet and forms a mating engagement with the outlet, wherein the locking mechanism is adapted to engage and retain the tip of the extension of the plunger assembly in a locked position at least partially within the passage of the outlet, wherein the locking mechanism comprises a plurality of flexible protrusions disposed about the inside surface of the outlet and extending into the passage, wherein the hub further comprises a tip extending from the distal end of the cylindrical skirt portion, the tip of the hub having an orifice extending therethrough in fluid communication with an interior of the cylindrical skirt portion such that the orifice is in fluid communication with the passage of the outlet, and a plug portion extending proximally within the cylindrical skirt portion from the distal end of the cylindrical skirt portion so as to form an annular recess between the plug portion and the cylindrical skirt portion, the annular recess being shaped to correspond to the distal end portion of the outlet and the orifice of the tip of the hub extending through the plug portion, and wherein the plug portion of the hub extends into the passage of the outlet of the syringe so as to close the passage and to cause the distal end portion of the outlet to engage the hub within the annular recess in a secured mating engagement.

* * * * *